(12) United States Patent
Struck et al.

(10) Patent No.: US 10,024,872 B2
(45) Date of Patent: Jul. 17, 2018

(54) AUGURIN IMMUNOASSAY

(71) Applicant: B.R.A.H.M.S. GMBH, Hennigsdorf (DE)

(72) Inventors: Joachim Struck, Berlin (DE); Tim Ziera, Berlin (DE)

(73) Assignee: B.R.A.H.M.S GmbH, Hennigsdorf (DE)

( * ) Notice: Subject to any disclaimer, the term of this patent is extended or adjusted under 35 U.S.C. 154(b) by 0 days.

(21) Appl. No.: 14/903,893

(22) PCT Filed: Jul. 10, 2014

(86) PCT No.: PCT/EP2014/064840
§ 371 (c)(1),
(2) Date: Jan. 8, 2016

(87) PCT Pub. No.: WO2015/004248
PCT Pub. Date: Jan. 15, 2015

(65) Prior Publication Data
US 2016/0146840 A1 May 26, 2016

(30) Foreign Application Priority Data
Jul. 12, 2013 (EP) ..................................... 13176350

(51) Int. Cl.
G01N 33/573 (2006.01)
G01N 33/74 (2006.01)
C07K 16/26 (2006.01)
C12N 5/12 (2006.01)

(52) U.S. Cl.
CPC .............. *G01N 33/74* (2013.01); *C07K 16/26* (2013.01); *C12N 5/12* (2013.01); *C07K 2317/34* (2013.01); *G01N 2333/575* (2013.01)

(58) Field of Classification Search
None
See application file for complete search history.

(56) References Cited

FOREIGN PATENT DOCUMENTS

| WO | 0000610 A2 | 1/2000 |
|---|---|---|
| WO | 0012708 A2 | 3/2000 |
| WO | 0166748 A2 | 9/2001 |
| WO | 02100898 A2 | 12/2002 |
| WO | 2004097030 A2 | 11/2004 |
| WO | 2008014410 A2 | 1/2008 |
| WO | WO2008/014410 | * 1/2008 |
| WO | WO2008014410 | * 1/2008 |

OTHER PUBLICATIONS

ABCAM online published protocol, Sandwich ELISA, Jul. 2007.*
Baird, Andrew et al., "Cell surface localization and release of the candidate tumor suppressor Ecrg4 from polymorphonuclear cells and monocytes activate macrophages", Journal of Leukocyte Biology, May 2012, pp. 1-9, vol. 91.
Dang, Xitong et al., "Cell-specific processing and release of the hormone-like precursor and cadidate tumor suppressor gene product, Ecrg4", Cell Tissue Res, Apr. 18, 2012.
Donahue, John E. et al., "ECRG-4 expression in normal and neoplastic choroid plexus", Cerebrospinal Fluid Research, Jul. 7-10, 2010, Oral Presentation—54th Annual Meeting of the Society for Research into Hydrocephalus and Spina Bifida.
Gotze, Silke et al., "ECRG4 is a candidate tumor suppressor gene frequently hypermethylated in colorectal carcinoma and glioma", BMC Cancer, Dec. 17, 2009, pp. 1-11, vol. 9, No. 447.
Gonzalez, Ana et al., "Ecrg4 expression and its product augurin in the choroid plexus: impact on fetal brain development, cerebrospinal fluid homeostasis and neuroprogenitor cell response to CNS injury", Fluids and Barriers of the CNS, Jan. 18, 2011, pp. 1-17, vol. 8, No. 6.
Holtta, Mikko et al., "Peptidome Analysis of Cerebrospinal Fluid by LC-MALDI MS", PLoS ONE, Aug. 2012, pp. 1-11, vol. 7, No. 8.
Huh, Yuri Hyun et al., "Esophageal cancer related gene 4 (ECRG4) is a marker of articular chondrocyte differentiation and cartilage destruction", Gene, Sep. 6, 2009, pp. 7-15, vol. 448.
Kujuro, Yuki et al., "Esophageal cancer-related gene 4 is a secreted inducer of cell senescence expressed by aged CNS precursor cells", PNAS, May 4, 2010, pp. 8259-8264, vol. 107, No. 18.
Kurabi, Arwa et al., "Ecrg4 Attenuates the Inflammatory Proliferative Response of Mucosal Epithelial Cells to Infection", PLOS ONE, Apr. 2013, pp. 1-9, vol. 8, No. 4.
Mirabeau, Olivier et al., "Identification of novel peptide hormones in the human proteome by hidden Markov model screening", Genome Research, Feb. 6, 2007, pp. 320-327, vol. 17.
Mori, Yoichiro et al., "Expression of ECRG4 is an independent prognostic factor for poor survival in patients with esophageal squamous cell carcinoma", Oncology Reports, 2007, pp. 981-985, vol. 18.
Ozawa, Akihiko et al., "Processing of Proaugurin Is Required to Suppress Proliferation of Tumor Cell Lines", Molecular Endocrinology, Mar. 24, 2011, pp. 776-784.
Podvin, Sonia et al., "Esophageal Cancer Related Gene-4 Is a Choroid Plexus-Derived Injury Response Gene: Evidence for a Biphasic Response in Early and Late Brain Injury", PLoS ONE, Sep. 2011, pp. 1-9, vol. 6, No. 9.
Sabatier, Renaud et al., "Down-Regulation of ECRG4, a Candidate Tumor Suppressor Gene, in Human Breast Cancer", PLoS One, Nov. 2011: pp. 1-8, vol. 6, No. 11.

(Continued)

*Primary Examiner* — Lei Yao
(74) *Attorney, Agent, or Firm* — McBee Moore Woodward & Vanik IP, LLC; Susan McBee; Chester Moore

(57) ABSTRACT

The present invention relates to an immunoassay method for the detection of augurin or a precursor or fragment thereof comprising contacting a sample suspected of comprising augurin or a precursor or fragment thereof with a first and second antibody specific for augurin or a precursor or fragment thereof, wherein said first and second antibodies or antigen-binding fragments or derivatives thereof are specific for epitopes comprised in the sequence spanning amino acids 71 to 107 of pre-augurin according to SEQ ID NO:1.

10 Claims, 9 Drawing Sheets

(56) References Cited

OTHER PUBLICATIONS

Steck, Eric et al., "Enhanced expression of the human chitinase 3-like 2 gene (YKL-39) but not chitinase 3-like 1 gene (YKL-40) in osteoarthritic cartilage", Biochemical and Biophysical Research Communications, Oct. 15, 2002, pp. 109-115, vol. 299.

Tadross, JA et al., "Augurin stimulates the hypothalamo-pituitary-adrenal axis via the release of corticotrophin-releasing factor in rats", British Journal of Pharmacology, 2010, pp. 1663-1671, vol. 159.

Vanaja, Donkena Krishna et al., "Hypermethylation of Genes for Diagnosis and Risk Stratification of Prostate Cancer", National Institute of Health, Jun. 2009, pp. 549-560, vol. 27, No. 5.

Yue, Chun-Mei et al., "Expression of ECRG4, a novel esophageal cancer-related gene, downregulated by CpG island hypermethylation in human esophageal squamous cell carcinoma", World Journal of Gastroenterology, 2003, pp. 1174-1178, vol. 9, No. 6.

International Search Report and Written Opinion of the International Searching Authority dated Jan. 23, 2015, issued in PCT/EP2014/064840.

Certification of the International Depositary Authority DSMZ, Jul. 3, 2013, Accession No. ACC3206.

Certification of the International Depositary Authority DSMZ, Jul. 3, 2013, Accession No. ACC3207.

Certification of the International Depositary Authority DSMZ, Jul. 3, 2013, Accession No. ACC3208.

Certification of the International Depositary Authority DSMZ, Jul. 3, 2013, Accession No. ACC3209.

Certification of the International Depositary Authority DSMZ, Jul. 3, 2013, Accession No. ACC3210.

Certification of the International Depositary Authority DSMZ, Jul. 3, 2013, Accession No. ACC3211.

* cited by examiner

A

B

C

SEQUENCE LISTING

<160> NUMBER OF SEQ ID NOS: 37

<210> SEQ ID NO 1
<211> LENGTH: 148
<212> TYPE: PRT
<213> ORGANISM: Homo sapiens
<220> FEATURE:
<221> NAME/KEY: MISC_FEATURE
<222> LOCATION: (1)..(148)
<223> OTHER INFORMATION: amino acid sequence of pre-augurin

<400> SEQUENCE: 1

Met Ala Ala Ser Pro Ala Arg Pro Ala Val Leu Ala Leu Thr Gly Leu
1               5                   10                  15

Ala Leu Leu Leu Leu Cys Trp Gly Pro Gly Gly Ile Ser Gly Asn
            20                  25                  30

Lys Leu Lys Leu Met Leu Gln Lys Arg Glu Ala Pro Val Pro Thr Lys
        35                  40                  45

Thr Lys Val Ala Val Asp Glu Asn Lys Ala Lys Glu Phe Leu Gly Ser
    50                  55                  60

Leu Lys Arg Gln Lys Arg Gln Leu Trp Asp Arg Thr Arg Pro Glu Val
65                  70                  75                  80

Gln Gln Trp Tyr Gln Gln Phe Leu Tyr Met Gly Phe Asp Glu Ala Lys
                85                  90                  95

Phe Glu Asp Asp Ile Thr Tyr Trp Leu Asn Arg Asp Arg Asn Gly His
            100                 105                 110

Glu Tyr Tyr Gly Asp Tyr Tyr Gln Arg His Tyr Asp Glu Asp Ser Ala
        115                 120                 125

Ile Gly Pro Arg Ser Pro Tyr Gly Phe Arg His Gly Ala Ser Val Asn
    130                 135                 140

Tyr Asp Asp Tyr
145

<210> SEQ ID NO 2
<211> LENGTH: 118
<212> TYPE: PRT
<213> ORGANISM: Homo sapiens
<220> FEATURE:
<221> NAME/KEY: MISC_FEATURE
<222> LOCATION: (1)..(118)
<223> OTHER INFORMATION: amino acid sequence of augurin

<400> SEQUENCE: 2

Gly Asn Lys Leu Lys Leu Met Leu Gln Lys Arg Glu Ala Pro Val Pro
1               5                   10                  15

Thr Lys Thr Lys Val Ala Val Asp Glu Asn Lys Ala Lys Glu Phe Leu
            20                  25                  30

```
Gly Ser Leu Lys Arg Gln Lys Arg Gln Leu Trp Asp Arg Thr Arg Pro
            35                  40                  45
Glu Val Gln Gln Trp Tyr Gln Gln Phe Leu Tyr Met Gly Phe Asp Glu
 50                  55                  60
Ala Lys Phe Glu Asp Asp Ile Thr Tyr Trp Leu Asn Arg Asp Arg Asn
 65                  70                  75                  80
Gly His Glu Tyr Tyr Gly Asp Tyr Tyr Gln Arg His Tyr Asp Glu Asp
                    85                  90                  95
Ser Ala Ile Gly Pro Arg Ser Pro Tyr Gly Phe Arg His Gly Ala Ser
                100                 105                 110
Val Asn Tyr Asp Asp Tyr
                115

<210> SEQ ID NO 3
<211> LENGTH: 38
<212> TYPE: PRT
<213> ORGANISM: Homo sapiens
<220> FEATURE:
<221> NAME/KEY: MISC_FEATURE
<222> LOCATION: (1)..(38)
<223> OTHER INFORMATION: amino acid sequence of ecilin

<400> SEQUENCE: 3

Gly Asn Lys Leu Lys Leu Met Leu Gln Lys Arg Glu Ala Pro Val Pro
 1               5                  10                  15
Thr Lys Thr Lys Val Ala Val Asp Glu Asn Lys Ala Lys Glu Phe Leu
                20                  25                  30
Gly Ser Leu Lys Arg Gln
                35

<210> SEQ ID NO 4
<211> LENGTH: 78
<212> TYPE: PRT
<213> ORGANISM: Homo sapiens
<220> FEATURE:
<221> NAME/KEY: MISC_FEATURE
<222> LOCATION: (1)..(78)
<223> OTHER INFORMATION: amino acid sequence of argilin

<400> SEQUENCE: 4

Gln Leu Trp Asp Arg Thr Arg Pro Glu Val Gln Gln Trp Tyr Gln Gln
 1               5                  10                  15
Phe Leu Tyr Met Gly Phe Asp Glu Ala Lys Phe Glu Asp Asp Ile Thr
                20                  25                  30
Tyr Trp Leu Asn Arg Asp Arg Asn Gly His Glu Tyr Tyr Gly Asp Tyr
                35                  40                  45
Tyr Gln Arg His Tyr Asp Glu Asp Ser Ala Ile Gly Pro Arg Ser Pro
 50                  55                  60
Tyr Gly Phe Arg His Gly Ala Ser Val Asn Tyr Asp Asp Tyr
 65                  70                  75

<210> SEQ ID NO 5
<211> LENGTH: 15
<212> TYPE: PRT
<213> ORGANISM: Homo sapiens
<220> FEATURE:
<221> NAME/KEY: MISC_FEATURE
<222> LOCATION: (1)..(15)
<223> OTHER INFORMATION: amino acid sequence 16

<400> SEQUENCE: 5
```

```
Pro Tyr Gly Phe Arg His Gly Ala Ser Val Asn Tyr Asp Asp Tyr
1               5                   10                  15
```

<210> SEQ ID NO 6
<211> LENGTH: 103
<212> TYPE: PRT
<213> ORGANISM: Homo sapiens
<220> FEATURE:
<221> NAME/KEY: MISC_FEATURE
<222> LOCATION: (1)..(103)
<223> OTHER INFORMATION: amino acid sequence of 16-augurin

<400> SEQUENCE: 6

```
Gly Asn Lys Leu Lys Leu Met Leu Gln Lys Arg Glu Ala Pro Val Pro
1               5                   10                  15

Thr Lys Thr Lys Val Ala Val Asp Glu Asn Lys Ala Lys Glu Phe Leu
            20                  25                  30

Gly Ser Leu Lys Arg Gln Lys Arg Gln Leu Trp Asp Arg Thr Arg Pro
        35                  40                  45

Glu Val Gln Gln Trp Tyr Gln Gln Phe Leu Tyr Met Gly Phe Asp Glu
    50                  55                  60

Ala Lys Phe Glu Asp Asp Ile Thr Tyr Trp Leu Asn Arg Asp Arg Asn
65                  70                  75                  80

Gly His Glu Tyr Tyr Gly Asp Tyr Tyr Gln Arg His Tyr Asp Glu Asp
                85                  90                  95

Ser Ala Ile Gly Pro Arg Ser
            100
```

<210> SEQ ID NO 7
<211> LENGTH: 63
<212> TYPE: PRT
<213> ORGANISM: Homo sapiens
<220> FEATURE:
<221> NAME/KEY: MISC_FEATURE
<222> LOCATION: (1)..(63)
<223> OTHER INFORMATION: amino acid sequence of 16-argilin

<400> SEQUENCE: 7

```
Gln Leu Trp Asp Arg Thr Arg Pro Glu Val Gln Gln Trp Tyr Gln Gln
1               5                   10                  15

Phe Leu Tyr Met Gly Phe Asp Glu Ala Lys Phe Glu Asp Asp Ile Thr
            20                  25                  30

Tyr Trp Leu Asn Arg Asp Arg Asn Gly His Glu Tyr Tyr Gly Asp Tyr
        35                  40                  45

Tyr Gln Arg His Tyr Asp Glu Asp Ser Ala Ile Gly Pro Arg Ser
    50                  55                  60
```

<210> SEQ ID NO 8
<211> LENGTH: 13
<212> TYPE: PRT
<213> ORGANISM: Artificial Sequence
<220> FEATURE:
<223> OTHER INFORMATION: amino acid sequence of PKE14

<400> SEQUENCE: 8

```
Lys Thr Lys Val Ala Val Asp Glu Asn Lys Ala Lys Glu
1               5                   10
```

<210> SEQ ID NO 9
<211> LENGTH: 13
<212> TYPE: PRT
<213> ORGANISM: Artificial Sequence
<220> FEATURE:

```
<223> OTHER INFORMATION: amino acid sequence of PQW14

<400> SEQUENCE: 9

Gln Leu Trp Asp Arg Thr Arg Pro Glu Val Gln Gln Trp
1               5                   10

<210> SEQ ID NO 10
<211> LENGTH: 10
<212> TYPE: PRT
<213> ORGANISM: Artificial Sequence
<220> FEATURE:
<223> OTHER INFORMATION: amino acid sequence of AUG-EL10

<400> SEQUENCE: 10

Glu Val Gln Gln Trp Tyr Gln Gln Phe Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: amino acid sequence of PGY14

<400> SEQUENCE: 11

Gly Phe Asp Glu Ala Lys Phe Glu Asp Asp Ile Thr Tyr
1               5                   10

<210> SEQ ID NO 12
<211> LENGTH: 13
<212> TYPE: PRT
<213> ORGANISM: Artificial Sequence
<220> FEATURE:
<223> OTHER INFORMATION: amino acid sequence of PDI14

<400> SEQUENCE: 12

Asp Tyr Tyr Gln Arg His Tyr Asp Glu Asp Ser Ala Ile
1               5                   10

<210> SEQ ID NO 13
<211> LENGTH: 6
<212> TYPE: PRT
<213> ORGANISM: Artificial Sequence
<220> FEATURE:
<223> OTHER INFORMATION: amino acid sequence 73-78 of pre-augurin

<400> SEQUENCE: 13

Trp Asp Arg Thr Arg Pro
1               5

<210> SEQ ID NO 14
<211> LENGTH: 6
<212> TYPE: PRT
<213> ORGANISM: Artificial Sequence
<220> FEATURE:
<223> OTHER INFORMATION: amino acid sequence 82-87 of pre-augurin

<400> SEQUENCE: 14

Gln Trp Tyr Gln Gln Phe
1               5

<210> SEQ ID NO 15
<211> LENGTH: 5
<212> TYPE: PRT
<213> ORGANISM: Artificial Sequence
<220> FEATURE:
<223> OTHER INFORMATION: amino acid sequence 83-87 of pre-augurin
```

```
<400> SEQUENCE: 15

Trp Tyr Gln Gln Phe
1               5

<210> SEQ ID NO 16
<211> LENGTH: 61
<212> TYPE: PRT
<213> ORGANISM: Artificial Sequence
<220> FEATURE:
<223> OTHER INFORMATION: amino acid sequence of PQD-61

<400> SEQUENCE: 16

Gln Leu Trp Asp Arg Thr Arg Pro Glu Val Gln Gln Trp Tyr Gln Gln
1               5                  10                  15

Phe Leu Tyr Met Gly Phe Asp Glu Ala Lys Phe Glu Asp Asp Ile Thr
            20                  25                  30

Tyr Trp Leu Asn Arg Asp Arg Asn Gly His Glu Tyr Tyr Gly Asp Tyr
        35                  40                  45

Tyr Gln Arg His Tyr Asp Glu Asp Ser Ala Ile Gly Pro
    50                  55                  60

<210> SEQ ID NO 17
<211> LENGTH: 15
<212> TYPE: PRT
<213> ORGANISM: Artificial Sequence
<220> FEATURE:
<223> OTHER INFORMATION: amino acid sequence of AUG-WF15

<400> SEQUENCE: 17

Trp Asp Arg Thr Arg Pro Glu Val Gln Gln Trp Tyr Gln Gln Phe
1               5                  10                  15

<210> SEQ ID NO 18
<211> LENGTH: 16
<212> TYPE: PRT
<213> ORGANISM: Artificial Sequence
<220> FEATURE:
<223> OTHER INFORMATION: amino acid sequence 71-86 of pre-augurin

<400> SEQUENCE: 18

Gln Leu Trp Asp Arg Thr Arg Pro Glu Val Gln Gln Trp Tyr Gln Gln
1               5                  10                  15

<210> SEQ ID NO 19
<211> LENGTH: 14
<212> TYPE: PRT
<213> ORGANISM: Artificial Sequence
<220> FEATURE:
<223> OTHER INFORMATION: amino acid sequence 73-86 of pre-augurin

<400> SEQUENCE: 19

Trp Asp Arg Thr Arg Pro Glu Val Gln Gln Trp Tyr Gln Gln
1               5                  10

<210> SEQ ID NO 20
<211> LENGTH: 13
<212> TYPE: PRT
<213> ORGANISM: Artificial Sequence
<220> FEATURE:
<223> OTHER INFORMATION: amino acid sequence 74-86 of pre-augurin

<400> SEQUENCE: 20

Asp Arg Thr Arg Pro Glu Val Gln Gln Trp Tyr Gln Gln
1               5                  10
```

<210> SEQ ID NO 21
<211> LENGTH: 12
<212> TYPE: PRT
<213> ORGANISM: Artificial Sequence
<220> FEATURE:
<223> OTHER INFORMATION: amino acid sequence 75-86 of pre-augurin

<400> SEQUENCE: 21

Arg Thr Arg Pro Glu Val Gln Gln Trp Tyr Gln Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: amino acid sequence 76-86 of pre-augurin

<400> SEQUENCE: 22

Thr Arg Pro Glu Val Gln Gln Trp Tyr Gln Gln
1               5                   10

<210> SEQ ID NO 23
<211> LENGTH: 15
<212> TYPE: PRT
<213> ORGANISM: Artificial Sequence
<220> FEATURE:
<223> OTHER INFORMATION: amino acid sequence 68-82 of pre-augurin

<400> SEQUENCE: 23

Gln Lys Arg Gln Leu Trp Asp Arg Thr Arg Pro Glu Val Gln Gln
1               5                   10                  15

<210> SEQ ID NO 24
<211> LENGTH: 14
<212> TYPE: PRT
<213> ORGANISM: Artificial Sequence
<220> FEATURE:
<223> OTHER INFORMATION: amino acid sequence 68-81 of pre-augurin

<400> SEQUENCE: 24

Gln Lys Arg Gln Leu Trp Asp Arg Thr Arg Pro Glu Val Gln
1               5                   10

<210> SEQ ID NO 25
<211> LENGTH: 13
<212> TYPE: PRT
<213> ORGANISM: Artificial Sequence
<220> FEATURE:
<223> OTHER INFORMATION: amino acid sequence 68-80 of pre-augurin

<400> SEQUENCE: 25

Gln Lys Arg Gln Leu Trp Asp Arg Thr Arg Pro Glu Val
1               5                   10

<210> SEQ ID NO 26
<211> LENGTH: 12
<212> TYPE: PRT
<213> ORGANISM: Artificial Sequence
<220> FEATURE:
<223> OTHER INFORMATION: amino acid sequence 68-79 of pre-augurin

<400> SEQUENCE: 26

Gln Lys Arg Gln Leu Trp Asp Arg Thr Arg Pro Glu
1               5                   10

```
<210> SEQ ID NO 27
<211> LENGTH: 13
<212> TYPE: PRT
<213> ORGANISM: Artificial Sequence
<220> FEATURE:
<223> OTHER INFORMATION: amino acid sequence 76-88 of pre-augurin

<400> SEQUENCE: 27

Thr Arg Pro Glu Val Gln Gln Trp Tyr Gln Gln Phe Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: amino acid sequence 76-87 of pre-augurin

<400> SEQUENCE: 28

Thr Arg Pro Glu Val Gln Gln Trp Tyr Gln Gln Phe
1               5                   10

<210> SEQ ID NO 29
<211> LENGTH: 10
<212> TYPE: PRT
<213> ORGANISM: Artificial Sequence
<220> FEATURE:
<223> OTHER INFORMATION: amino acid sequence 76-85 of pre-augurin

<400> SEQUENCE: 29

Thr Arg Pro Glu Val Gln Gln Trp Tyr Gln
1               5                   10

<210> SEQ ID NO 30
<211> LENGTH: 9
<212> TYPE: PRT
<213> ORGANISM: Artificial Sequence
<220> FEATURE:
<223> OTHER INFORMATION: amino acid sequence 76-84 of pre-augurin

<400> SEQUENCE: 30

Thr Arg Pro Glu Val Gln Gln Trp Tyr
1               5

<210> SEQ ID NO 31
<211> LENGTH: 8
<212> TYPE: PRT
<213> ORGANISM: Artificial Sequence
<220> FEATURE:
<223> OTHER INFORMATION: amino acid sequence 76-83 of pre-augurin

<400> SEQUENCE: 31

Thr Arg Pro Glu Val Gln Gln Trp
1               5

<210> SEQ ID NO 32
<211> LENGTH: 13
<212> TYPE: PRT
<213> ORGANISM: Artificial Sequence
<220> FEATURE:
<223> OTHER INFORMATION: amino acid sequence 79-91 of pre-augurin

<400> SEQUENCE: 32

Glu Val Gln Gln Trp Tyr Gln Gln Phe Leu Tyr Met Gly
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: amino acid sequence 80-91 of pre-augurin

<400> SEQUENCE: 33

Val Gln Gln Trp Tyr Gln Gln Phe Leu Tyr Met Gly
1               5                   10

<210> SEQ ID NO 34
<211> LENGTH: 11
<212> TYPE: PRT
<213> ORGANISM: Artificial Sequence
<220> FEATURE:
<223> OTHER INFORMATION: amino acid sequence 81-91 of pre-augurin

<400> SEQUENCE: 34

Gln Gln Trp Tyr Gln Gln Phe Leu Tyr Met Gly
1               5                   10

<210> SEQ ID NO 35
<211> LENGTH: 10
<212> TYPE: PRT
<213> ORGANISM: Artificial Sequence
<220> FEATURE:
<223> OTHER INFORMATION: amino acid sequence 82-91 of pre-augurin

<400> SEQUENCE: 35

Gln Trp Tyr Gln Gln Phe Leu Tyr Met Gly
1               5                   10

<210> SEQ ID NO 36
<211> LENGTH: 9
<212> TYPE: PRT
<213> ORGANISM: Artificial Sequence
<220> FEATURE:
<223> OTHER INFORMATION: amino acid sequence 83-91 of pre-augurin

<400> SEQUENCE: 36

Trp Tyr Gln Gln Phe Leu Tyr Met Gly
1               5

<210> SEQ ID NO 37
<211> LENGTH: 8
<212> TYPE: PRT
<213> ORGANISM: Artificial Sequence
<220> FEATURE:
<223> OTHER INFORMATION: amino acid sequence 84-91 of pre-augurin

<400> SEQUENCE: 37

Tyr Gln Gln Phe Leu Tyr Met Gly
1               5
```

AUGURIN IMMUNOASSAY

CROSS REFERENCE TO RELATED APPLICATIONS

This application is a § 371 National Stage Application of PCT/EP2014/064840 filed 10 Jul. 2014, which claims priority to EP 13176350.0, filed 12 Jul. 2013.

BACKGROUND

Field of the Invention

The present invention is in the field of immunoassays. Particularly, the present invention relates to the determination of the level of augurin or precursors or fragments thereof in a sample derived from a bodily fluid or tissue of a subject.

Description of Related Art

Augurin, a recently identified secreted peptide, is encoded by esophageal cancer related gene-4 (ECRG4) and conserved among vertebrates (Mirabeau et al. 2007. *Genome Research* 17: 320-327). Human ECRG4 encodes a 148 amino acid protein, which contains a leader peptide at residues 1-30. One processed form of the protein encoded by ECRG4 has been termed augurin (residues 31-148) but a single putative pro-hormone cleavage site at residues 68-71 yields two putative peptide hormones that have been named ecilin (residues 31-70), after the EC part of ECRG4, and the fragment 71-148 as argilin, after the RG part of ECRG4 (Gonzalez et al. 2011. *Fluids and Barriers of the CNS.* 8:6). A second predicted proteolytic consensus site for thrombin cleavage generates C-terminal Δ16 sequences when incubated with thrombin (amino acid residues 134-148). In addition, augurin-dimers were also noted (Gonzalez et al. 2011. *Fluids and Barriers of the CNS.* 8:6).

Examinations of posttranslational modifications of augurin in mouse pituitary adenoma and human colon carcinoma cells revealed that it is cleaved by the enzyme furin and secreted via the constitutive secretory pathway (Ozawa et al. 2011. *Molecular Endocrinology* 25(5): 776-784). In addition, augurin is sulfated during trafficking and proteolytic cleavage (at $R^{41}E^{42}$ and/or $R^{70}Q^{71}$), which is a posttranslational requirement for augurin to suppress cell proliferation.

Dang et al. 2012 found that ECRG4 was localized to the epithelial surface of human cells (Dane et al. 2012. *Cell Tissue Research* 348(3): 505-514) and speculated that the release of ECRG4 is cell-specific and tissue-specific processing may control different ECRG4 activities in different tissues.

ECRG4 shows a tissue-specific expression in human heart, brain, placenta, lung, liver, skeletal muscle, kidney and pancreas with the strongest expression detected in heart and kidney (Steck et al. 2002. *Biochemical and Biophysical Research Communications* 299: 109-115). In regions of the brain ECGR4 was mainly found in the hypothalamus and choroid plexus epithelial cells (Tadross et al. 2010. *British Journal of Pharmacology* 159: 1663-1671: Donahue et al. 2010. *Cerebrospinal Fluid Research* 7(Suppl 1):S32; Gonzalez et al. 2011. *Fluids and Barriers of the CNS* 8:6). After injury of the central nervous system (CNS) in the rat, a rapid loss of augurin and ECRG4 gene expression was detected in choroid plexus epithelia with an immediate mobilization of augurin after CNS injury that was presumably released into cerebrospinal fluid (CSF) (Podvin et al. 2011. *PLoS One* 6(9): e24609). In human CSF the augurin precursor was identified as an endogenous peptide (Hoelttae et al. 2012. *PLoS One* 7(8): e42555).

It was shown that augurin stimulates the release of ACTH via release of hypothalamic CRF and might be a novel therapeutic target for the regulation of the hypothalamo-pituitary-adrenal axis (Tadross et al. 2010. *British Journal of Pharmacology* 159: 1663-1671). Moreover, ECRG4 expression was particularly abundant in chondrocytes and cartilage with a dramatic increase during chondrogenic differentiation and a decrease in osteoarthritic cartilage, suggesting ECRG4 as a marker of differentiated articular chondrocytes and cartilage destruction (Huh et al. 2009. *Gene* 448:7-15).

ECRG4 seems to be implicated in neural cell-senescence and aging in the brain of adult mice (Kujuro et al. 2010. *PNAS* 107(18): 8259-8264).

The ECRG4 gene is down-regulated by hypermethylation in different cancers (e.g. esophageal squamous cell carcinoma [ESCC], prostate cancer, colorectal carcinoma, malignant glioma and gastric cancer) suggesting that its epigenetic control plays a role in the transformation of normal cells to cancer (Yue et al. 2003. *World Journal of Gastroenterology* 9(6):1174-1178; Vanaja et al. 2009. *Cancer Investigation* 27(5): 549-560; Goetze et al. 2009. *BMC Cancer* 9: 447; Wang et al. 2012. *Hepatogastroenterology* 59(118):1696-1698). It was shown that hypermethylation of the ECRG4 gene was associated with the prediction of recurrence of prostate cancer (Vanaja et al. 2009. *Cancer Investigation* 27(5): 549-560) and might be used to monitor early gastric cancer and predict pathological staging (Wang et al. 2012. *Hepatogastroenterology* 59(118):1696-1698). Moreover, it was shown that ECRG4 mRNA expression level could be a candidate for an independent prognostic factor for ESCC patients, as it is correlated with local invasiveness, pathological stages and the prognosis of patients (Mori et al. *Oncology Reports* 18: 981-985; Li et al. 2009, *International Journal of Cancer:* 125, 1505-1513). Mori and colleagues further hypothesized that it might also be important in selecting only those patients for surgery who will benefit from it. ECRG4 mRNA expression was decreased in invasive breast cancer samples and correlated with stage and size (Sabatier et al. 2011 *PLoS ONE* 6(11): e27656). Furthermore, it is suggested as a prognostic factor as it was correlated with disease-free and overall survival of breast cancer patients.

ECRG4 mRNA was also elevated in human peripheral blood cells, but incubation with lipopolysaccharide (LPS) significantly decreased cell surface ECRG4 in polymorphonuclear cells and monocytes (Baird et al. 2012. *Journal of Leucocyte Biology* 91(5): 773-781). In conditioned media of LPS-treated leukocytes 14 kDa ECRG4 and 8 kDa ECRG4 (corresponding to ECRG4 71-148) were detected. Lower ECRG4 expression levels on leukocytes could be associated with injury in patients with TBSA burn, a systemic inflammatory response syndrome [SIRS] and injured blunt trauma patients suggesting a clinical relevance for ECRG4 in the biology of injury and involvement in the inflammatory response. However, ECRG4 expression was not detectable in blood (Baird et al. 2012. *Journal of Leucocyte Biology* 91(5): 773-781). It was additionally shown that upon experimental middle ear infection of rats, ECRG4 expression rapidly decreased between 3-48 hours post-infection in rat mucosal tissue (Kurabi et al. 2013—*PLoS One* 8(4): e61394).

A competitive enzyme immunoassay for the detection of human prepro-(71-107)-augurin is available from Phoenix Pharmaceuticals Inc, Burlingame Calif., USA. However, there is a need for an improved assay for the detection of augurin and fragments and precursors thereof with a high sensitivity and specificity as well as a high reproducibility and low inter-assay variation. The present invention provides such an assay which can, e.g., be used as a research tool for the detection of augurin at low concentrations and with a high specificity.

SUMMARY

Subject of the invention is an immunoassay method for the detection of augurin or a precursor or fragment thereof. The method in one aspect comprises the steps of
  (a) contacting a sample suspected of comprising augurin or a precursor or fragment thereof with a first antibody or an antigen-binding fragment or derivative thereof specific for augurin or a precursor or fragment thereof and a second antibody or an antigen-binding fragment or derivative thereof specific for augurin or a precursor or fragment thereof under conditions allowing for the formation of a ternary complex between augurin or a precursor or fragment thereof under conditions allowing for the binding of the two antibodies or an antigen-binding fragment or derivative thereof to augurin or a precursor or fragment thereof, wherein said first and second antibodies or antigen-binding fragments or derivatives thereof are specific for epitopes comprised in the sequence spanning amino acids 71 to 107 of pre-augurin according to SEQ ID NO:1, and wherein said first and second antibodies or antigen-binding fragments or derivatives thereof are specific for different and non-overlapping epitopes, and
  (b) detecting the binding of the two antibodies or antigen-binding fragments or derivatives thereof to augurin or a precursor or fragment thereof.

The invention also relates to an immunoassay method for the detection of augurin or a precursor or fragment thereof comprising the steps of
  (a) contacting a sample suspected of comprising augurin or a precursor or fragment thereof with a first antibody or an antigen-binding fragment or derivative thereof specific for augurin or a precursor or fragment thereof under conditions allowing for the formation of a complex between augurin or a precursor or fragment thereof and said first antibody or antigen-binding fragment or derivative thereof,
  (b) contacting said sample with a second antibody or an antigen-binding fragment or derivative thereof specific for augurin or a precursor or fragment thereof under conditions allowing for the formation of a ternary complex between augurin or a precursor or fragment thereof and said first and second antibodies or antigen-binding fragments or derivatives thereof,
    wherein said first and second antibodies or antigen-binding fragments or derivatives thereof are specific for epitopes comprised in the sequence spanning amino acids 71 to 107 of pre-augurin according to SEQ ID NO:1,
    wherein said first and second antibodies or antigen-binding fragments or derivatives thereof are specific for different and non-overlapping epitopes, and
  (c) detecting said ternary complex.

The invention also relates to a kit for the detection of augurin or a precursor or fragment thereof comprising
  (i) an antibody or antigen-binding fragment or derivative thereof which is specific for an epitope comprised in the sequence spanning amino acids 71 to 107, preferably 71 to 88, more preferably 71 to 83 of pre-augurin according to SEQ ID NO:1; and
  (ii) an antibody or antigen-binding fragment or derivative thereof which is specific for an epitope comprised in the sequence spanning amino acids 71 to 107, preferably 71 to 88, more preferably 79 to 88 of pre-augurin according to SEQ ID NO:1.

Subject of the invention is further an anti-augurin antibody or an antigen-binding fragment or derivative thereof, wherein the antibody or fragment or derivative thereof is specific for an epitope comprised in the sequence spanning amino acids 71 to 107, preferably 71 to 88, more preferably 71 to 83 of pre-augurin according to SEQ ID NO:1 or is specific for an epitope comprised in the sequence spanning amino acids 79 to 88 of pre-augurin according to SEQ ID NO:1.

The invention further relates to a hybridoma cell line selected from cell line 439/F4 deposited as DSM ACC3206, cell line 439/H10 deposited as DSM ACC3207, cell line 482/H2 deposited as DSM ACC3208, cell line 482/H10 deposited as DSM ACC3209, cell line 482/H7 deposited as DSM ACC3210 and cell line 482/G9 deposited as DSM ACC3211.

Preferred method variants are described in the dependent claims.

DETAILED DESCRIPTION OF A PREFERRED EMBODIMENT

Figure 1:
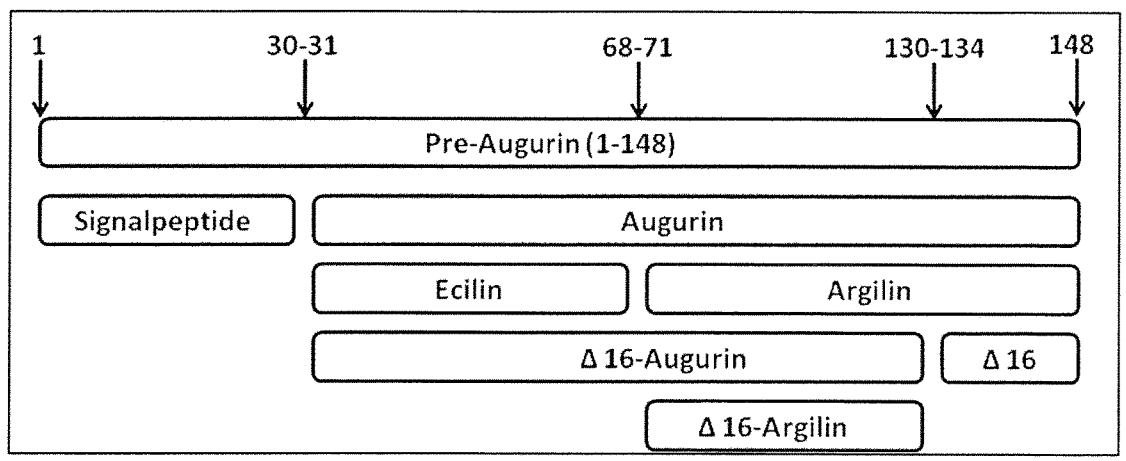
FIG. 1: Structure of pre-augurin and possible processed peptides

The present invention relates to an immunoassay for the detection of the augurin protein or a precursor peptide or peptide fragment thereof. Specifically, the immunoassay detects epitopes comprising amino acid residues 71 to 107, preferably amino acid residues 71 to 88 of the pre-augurin sequence according to SEQ ID NO: 1. Hence, fragments and precursors of augurin encompassing amino acid residues 71 to 107, preferably 71 to 88, of the pre-augurin sequence can be detected with the immunoassay provided herein. These fragments include argilin, Δ16-augurin and Δ16-argilin as outlined below (e.g. see FIG. 1). The immunoassay method of the invention is based on the surprising finding that a combination of two anti-augurin antibodies that are able to specifically bind to epitopes in the sequence spanning amino acids 71 to 107 of pre-augurin results in an improved detection of augurin (or fragments or precursors thereof comprising these epitopes). The immunoassay method of the invention makes use of two distinct anti-augurin antibodies that are able to specifically bind to epitopes in the sequence spanning amino acids 71 to 107, preferably 71 to 88, of pre-augurin according to SEQ ID NO:1. Augurin or a precursor or fragment thereof can according to the immunoassay of the invention be qualitatively and/or quantitatively be detected by the binding of the two antibodies to the augurin or precursor or fragment thereof. The presence of augurin or its fragment or precursors will be detected if both antibodies bind the augurin or its fragment or precursor. In other words the invention relates to an immunoassay for the detection of augurin or a precursor or fragment thereof in a sample comprising the steps of contacting said sample with a first anti-augurin antibody (or an antigen-binding fragment or derivative thereof) and a second anti-augurin antibody (or an antigen-binding fragment or derivative thereof) and detecting the presence of ternary immune complexes of said antibodies and augurin or a precursor or fragment thereof. The immune complexes will form under conditions that allow an immunoreaction between said antibodies and said sample.

The invention in one aspect relates to an immunoassay method for the detection of augurin or a precursor or fragment thereof comprising the steps of (a) contacting a sample suspected of comprising augurin or a precursor or fragment thereof with a first antibody or an antigen-binding fragment or derivative thereof specific for augurin or a precursor or fragment thereof and a second antibody or an antigen-binding fragment or derivative thereof specific for augurin or a precursor or fragment thereof under conditions allowing for the formation of a ternary complex between augurin or a precursor or fragment thereof under conditions allowing for the binding of the two antibodies or an antigen-binding fragment or derivative thereof to augurin or a precursor or fragment thereof,
wherein said first and second antibodies or antigen-binding fragments or derivatives thereof are specific for epitopes comprised in the sequence spanning amino acids 71 to 107 of pre-augurin according to SEQ ID NO:1, and
wherein said first and second antibodies or antigen-binding fragments or derivatives thereof are specific for different and non-overlapping epitopes, and
(b) detecting the binding of the two antibodies or antigen-binding fragments or derivatives thereof to augurin or a precursor or fragment thereof. The specific binding of the two antibodies or antigen-binding fragments or derivatives thereof is indicative for the presence of augurin or a precursor or fragment thereof.

The invention also pertains to an immunoassay method for the detection of augurin or a precursor or fragment thereof comprising the steps of (a) contacting a sample suspected of comprising augurin or a precursor or fragment thereof with a first antibody or an antigen-binding fragment or derivative thereof specific for augurin or a precursor or fragment thereof under conditions allowing for the formation of a complex between augurin or a precursor or fragment thereof and said first antibody or antigen-binding fragment or derivative thereof, (b) contacting said sample with a second antibody or an antigen-binding fragment or derivative thereof specific for augurin or a precursor or fragment thereof under conditions allowing for the formation of a ternary complex between augurin or a precursor or fragment thereof and said first and second antibodies or antigen-binding fragments or derivatives thereof,
wherein said first and second antibodies or antigen-binding fragments or derivatives thereof are specific for epitopes comprised in the sequence spanning amino acids 71 to 107 of pre-augurin according to SEQ ID NO:1,
wherein said first and second antibodies or antigen-binding fragments or derivatives thereof are specific for different and non-overlapping epitopes, and
(c) detecting said ternary complex. Detection of the ternary complex in the sample is indicative for the presence of augurin or a precursor or fragment thereof.

In the immunoassay method according to the invention said first and second antibodies or antigen-binding fragments or derivatives thereof are specific for epitopes comprised in the sequence spanning amino acids 71 to 107, preferably 71 to 100, more preferably 71 to 95, even more preferably 71 to 90, most preferably 71 to 88 of pre-augurin according to SEQ ID NO:1. The epitopes of the two antibodies may be overlapping epitopes or may be non-overlapping epitopes. For example, said epitopes of the two antibodies may preferably be not more than 6 amino acids apart, i.e. there are not more than 6 amino acid residues between the two epitopes in the augurin sequence. The epitopes can, e.g., be not more than 6, not more than 5, not more than 4, not more than 3, not more than 2 or not more than 1 amino acid apart. The epitopes can also be directly adjacent to each other, i.e. with no amino acid residues in between.

In some cases the first and second antibodies or antigen-binding fragments or derivatives thereof are specific for epitopes comprised in the sequence spanning amino acids 71 to 107 and the said epitopes of the two antibodies are not more than 6, 5, 4, 3, 2, 1 or 0 amino acids apart. The first and second antibodies or antigen-binding fragments or derivatives thereof may also be specific for epitopes comprised in the sequence spanning amino acids 71 to 100 and the said epitopes of the two antibodies are not more than 6, 5, 4, 3, 2, 1 or 0 amino acids apart. The first and second antibodies or antigen-binding fragments or derivatives thereof may also be specific for epitopes comprised in the sequence spanning amino acids 71 to 95 and the said epitopes of the two antibodies are not more than 6, 5, 4, 3, 2, 1 or 0 amino acids apart. The first and second antibodies or antigen-binding fragments or derivatives thereof may also be specific for epitopes comprised in the sequence spanning amino acids 71 to 90 and the said epitopes of the two antibodies are not more than 6, 5, 4, 3, 2, 1 or 0 amino acids apart. The first and second antibodies or antigen-binding fragments or derivatives thereof may also be specific for epitopes comprised in the sequence spanning amino acids 71 to 88 and the said epitopes of the two antibodies are not more than 6, 5, 4, 3, 2, 1 or 0 amino acids apart. In all these cases monoclonal antibodies are preferred.

It is particularly preferred that said first and second antibodies or antigen-binding fragments or derivatives thereof are specific for epitopes comprised in the sequence spanning amino acids 71 to 88 according to SEQ ID NO:1 and said epitopes are not more than 3 amino acids apart. For example, the first antibody or antigen-binding fragment or derivative thereof is specific for an epitope comprised in the sequence spanning amino acids 71 to 83 of pre-augurin according to SEQ ID NO:1 and the second antibody or antigen-binding fragment or derivative thereof is specific for an epitope comprised in the sequence spanning amino acids 79 to 88 of pre-augurin according to SEQ ID NO:1.

As will be discussed herein below in more detail the antibodies or antigen-binding fragments or derivatives thereof of the immunoassay method as described herein may for instance be polyclonal antibodies, monoclonal antibodies or genetically engineered monoclonal antibodies. It is preferred that both antibodies are monoclonal antibodies. For example the first antibody or antigen-binding fragment or derivative thereof is produced by a hybridoma cell line selected from cell line 482/H2 deposited as DSM ACC3208, cell line 482/H10 deposited as DSM ACC3209, cell line 482/H7 deposited as DSM ACC3210 or cell line 482/G9 deposited as DSM ACC3211. The second antibody or antigen-binding fragment or derivative thereof may, for example, be produced by a hybridoma cell line selected from cell line 439/F4 deposited as DSM ACC3206 or cell line 439/H10 deposited as DSM ACC3207. Preferably herein in the context of the immunoassay methods and kits of the invention, the first antibody is the antibody produced by hybridoma cell line 482/H7 and the second antibody is the antibody produced by hybridoma cell line 439/F4.

As outlined above, the immunoassay of the invention fragments and precursors of augurin encompassing amino acid residues 71 to 107, preferably 71 to 88, of the pre-augurin sequence can be detected. Hence, the invention provides an immunoassay method for the detection of argilin, an immunoassay method for the detection of Δ16-augurin and immunoassay method for the detection of Δ16-argilin.

The binding of the antibodies to augurin (or its precursors or fragments) takes place under suitable conditions (i.e. allowing for immunoreactions, i.e. binding of the antibodies to augurin on formation of immune complexes). Such conditions are known to the skilled person and standard formats of immunoassays as described below can be used. Such conditions will preferably be under physiologic temperature, pH and ionic strength and can take place in media such as, for example, phosphate buffered saline (PBS).

The preferred detection methods comprise immunoassays in various formats such as for instance radioimmunoassay (RIA), chemiluminescence- and fluorescence-immunoassays, Enzyme-linked immunoassays (ELISA), Luminex-based bead arrays, protein microarray assays, and rapid test formats such as for instance immunochromatographic strip tests.

The assays can be homogenous or heterogeneous assays, competitive and non-competitive assays. In a particularly preferred embodiment, the assay is in the form of a sandwich assay, which is a non-competitive immunoassay, wherein the analyte to be detected and/or quantified is bound to a first antibody and to a second antibody. The first antibody may, e.g., be bound to a solid phase, e.g. a bead, a surface of a well or other container, a chip or a strip, and the second antibody is an antibody which is labeled, e.g. with a dye, with a radioisotope, or a reactive or catalytically active moiety. The amount of labeled antibody bound to the analyte is then measured by an appropriate method. The general composition and procedures involved with "sandwich assays" are well-established and known to the skilled person (*The Immunoassay Handbook*, Ed. David Wild, Elsevier LTD, Oxford; 3rd ed. (May 2005), ISBN-13: 978-0080445267; Hultschig C et al., *Curr Opin Chem Biol.* 2006 February; 10(1):4-10. PMID: 16376134, incorporated herein by reference). Sandwich immunoassays can for example be designed as one-step assays or as two-step assays.

In a particularly preferred embodiment the assay comprises two antibody molecules (i.e. antibodies or antigen-binding fragments or derivatives thereof), preferably antibodies, which are both present as dispersions in a liquid reaction mixture, wherein a first labelling component is attached to the first antibody molecule, wherein said first labelling component is part of a labelling system based on fluorescence- or chemiluminescence-quenching or amplification, and a second labelling component of said marking system is attached to the second antibody molecule, so that upon binding of both antibody molecules to the analyte a measurable signal is generated that allows for the detection of the formed sandwich complexes in the solution comprising the sample.

Even more preferred, said labelling system comprises rare earth cryptates or rare earth chelates in combination with a fluorescence dye or chemiluminescence dye, in particular a dye of the cyanine type. In the context of the present invention, fluorescence based assays comprise the use of dyes, which may for instance be selected from the group comprising FAM (5- or 6-carboxyfluorescein), VIC, NED, Fluorescein, Fluoresceinisothiocyanate (FITC), IRD-700/800, Cyanine dyes, such as CY3, CY5, CY3.5, CY5.5, Cy7, Xanthen, 6-Carboxy-2',4',7',4,7-hexachlorofluorescein (HEX), TET, 6-Carboxy-4',5'-dichloro-2',7'-dimethodyfluorescein (JOE), N,N,N',N'-Tetramethyl-6-carboxyrhodamine (TAMRA), 6-Carboxy-X-rhodamine (ROX), 5-Carboxyrhodamine-6G (R6G5), 6-carboxyrhodamine-6G (RG6), Rhodamine, Rhodamine Green, Rhodamine Red, Rhodamine 110, BODIPY dyes, such as BODIPY TMR, Oregon Green, Coumarines such as Umbelliferone, Benzimides, such as Hoechst 33258; Phenanthridines, such as Texas Red, Yakima Yellow, Alexa Fluor, PET, Ethidiumbromide, Acridinium dyes, Carbazol dyes, Phenoxazine dyes, Porphyrine dyes, Polymethin dyes, and the like.

In the context of the present invention, chemiluminescence based assays comprise the use of dyes, based on the physical principles described for chemiluminescent materials in *Kirk-Othmer, Encyclopedia of chemical technology*, 4$^{th}$ ed., executive editor. J. I. Kroschwitz; editor. M. Howe-Grant. John Wiley & Sons. 1993, vol. 15, p. 518-562, incorporated herein by reference, including citations on pages 551-562. Preferred chemiluminescent dyes are acridiniumesters.

As mentioned herein, an "assay" can be of any type applied in the field of immonoassays. Such an assay may be based on the binding of an analyte to be detected to one or more capture probes (here antibody molecules, i.e. antibodies or antigen-binding fragments or derivatives thereof) with a certain affinity. Concerning the interaction between antibody molecules and target molecules or molecules of interest (i.e. augurin or precursors or fragments thereof), the affinity constant is in the range of $10^8$ to $10^{11}$ M$^{-1}$, preferably above $10^9$ M$^{-1}$.

The "sensitivity" of an assay relates to the proportion of actual positives which are correctly identified as such, i.e. the ability to identify positive results (true positives positive results/number of positives). Hence, the lower the concentrations of the analyte that can be detected with an assay, the more sensitive is the assay. The "specificity" of an assay relates to the proportion of negatives which are correctly identified as such, i.e. the ability to identify negative results (true negatives/negative results). For an antibody the "specificity" is defined as the ability of an individual antigen binding site to react with only one antigenic epitope. The binding behaviour of an antibody can also be characterized in terms of its "affinity" and its "avidity". The "affinity" of an antibody is a measure for the strength of the reaction between a single antigenic epitope and a single antigen binding site. The "avidity" of an antibody is a measure for the overall strength of binding between an antigen with many epitopes and multivalent antibodies.

In the context of the present invention, "antibody molecules" (herein also designated as "capture molecules") are molecules which may be used to bind target molecules or molecules of interest, i.e. analytes (i.e. in the context of the present invention the augurin) or precursors or fragments thereof, from a sample. Capture molecules must thus be shaped adequately, both spatially and in terms of surface features, such as surface charge, hydrophobicity, hydrophilicity, presence or absence of lewis donors and/or acceptors, to specifically bind the target molecules or molecules of interest. Hereby, the binding may for instance be mediated by ionic, van-der-Waals, pi-pi, sigma-pi, hydrophobic or hydrogen bond interactions or a combination of two or more of the aforementioned interactions between the capture molecules and the target molecules or molecules of interest. In the context of the present invention, capture molecules are antibody molecules. Preferably, the antibody molecules are antibodies, including fragments thereof with sufficient affinity to a target or molecule of interest, and including recombinant antibodies or recombinant antibody fragments, as well as chemically and/or biochemically modified derivatives of said antibodies or fragments derived from the variant chain with a length of at least 12 amino acids thereof.

The term "antibody" as used herein, unless indicated otherwise, is used broadly to refer to both, antibody molecules and a variety of antibody-derived molecules. Such antibody derived molecules comprise at least one variable region (either a heavy chain or a light chain variable region), as well as individual antibody light chains, individual antibody heavy chains, chimeric fusions between antibody chains and other molecules, and the like. Functional immunoglobulin fragments according to the present invention may be Fv, scFv, disulfide-linked Fv, Fab, and F(ab')2. Antibodies, or fragments thereof, of the present invention, can be used to establish an immunoassay to detect augurin and fragments thereof. The antibodies may for example be IgMs, IgDs, IgEs, IgAs or IgGs, preferably IgG1, IgG2, IgG2b, IgG3 or IgG4, most preferably IgG1 antibodies. Also encompassed by the term "antibody" are polyclonal antibodies, monoclonal antibodies ("mAbs"), preferably IgG$_1$ antibodies; chimeric monoclonal antibodies; humanized antibodies, genetically engineered monoclonal antibodies. Antibodies are selected through techniques including, for example, phage display to specifically bind to the molecule of interest contained in a sample. In this context the term "specific binding" refers to antibodies raised against the molecule of interest or a fragment thereof. An antibody is considered to be specific, if its affinity towards the molecule of interest or the aforementioned fragment thereof is at least preferably 50-fold higher, more preferably 100-fold higher, most preferably at least 1000-fold higher than towards other molecules comprised in a sample containing the molecule of interest. It is well known in the art how to make antibodies and to select antibodies with a given specificity. The inventive antibodies/antibody molecules can readily be recombinantly constructed and expressed. Inventive antibody molecules can easily be produced in sufficient quantities, inter alia, by recombinant methods known in the art, see, e.g. Bentley, Hybridoma 17 (1998), 559-567; Racher, Appl. Microbiol. Biotechnol. 40 (1994), 851-856; Samuelsson, Eur. J. Immunol. 26 (1996), 3029-3034.

Preferably herein, the antibody molecule is a full antibody (immunoglobulin, like an IgG1, an IgG2, an IgG2b, an IgG3, an IgG4, an IgA, an IgM, an IgD or an IgE), an F(ab)-, Fabc-, Fv-, Fab'-, F(ab')$_2$-fragment, a single-chain antibody, a chimeric antibody, a CDR-grafted antibody, a bivalent antibody-construct, an antibody-fusion protein or a synthetic antibody. Monoclonal antibodies are preferred.

The invention also relates to a kit for the detection of augurin or a precursor or fragment thereof comprising
  (i) an antibody or antigen-binding fragment or derivative thereof which is specific for an epitope comprised in the sequence spanning amino acids 71 to 107, preferably 71 to 88, more preferably 71 to 83 of pre-augurin according to SEQ ID NO:1; and
  (ii) an antibody or antigen-binding fragment or derivative thereof which is specific for an epitope comprised in the sequence spanning amino acids 71 to 107, preferably 71 to 88, more preferably 79 to 88 of pre-augurin according to SEQ ID NO:1. Preferably, the kit comprises
  (i) an antibody or antigen-binding fragment or derivative thereof which is specific for an epitope comprised in the sequence spanning amino acids 71 to 83 of pre-augurin according to SEQ ID NO: 1; and
  (ii) an antibody or antigen-binding fragment or derivative thereof which is specific for an epitope comprised in the sequence spanning amino acids 79 to 88 of pre-augurin according to SEQ ID NO:1. The antibodies are preferably monoclonal antibodies.

The invention further relates to the use of a kit according to the present invention in a sandwich immunoassay format for the detection and/or quantification of augurin or a fragment thereof in a biological sample from a bodily fluid. Such a fragment at least comprises a sequence spanning the two epitopes against which the two antibodies are directed, e.g. the kit can be used for the detection and/or quantification of augurin, argilin, Δ16-augurin and Δ16-argilin.

As mentioned herein the term "fragment" refers to smaller proteins or peptides derivable from larger proteins or peptides, which hence comprise a partial sequence of the larger protein or peptide. Said fragments are derivable from the larger proteins or peptides by saponification of one or more of its peptide bonds.

The term "sample" is preferably a biological sample. "Sample" as used herein may, e.g., refer to a sample of bodily fluid or tissue obtained for the purpose of diagnosis, prognosis, or evaluation of a subject of interest, such as a patient. A "patient" or "subject" for the purposes of the present invention includes both humans and other animals, particularly mammals, and other organisms. Thus, the methods are applicable to both human diagnostics and veterinary applications. In a preferred embodiment the patient is a mammal, and in the most preferred embodiment the patient or subject is a human.

Preferred test samples include blood, serum, plasma, cerebrospinal fluid, urine, saliva, sputum, and pleural effusions. In addition, one of skill in the art would realize that some test samples would be more readily analyzed following a fractionation or purification procedure, for example, separation of whole blood into serum or plasma components.

Thus, in a preferred embodiment of the invention the sample is selected from the group comprising a blood sample, a serum sample, a plasma sample, a cerebrospinal fluid sample, a saliva sample and a urine sample or an extract of any of the aforementioned samples. Preferably, the sample is a blood sample, most preferably a serum sample or a plasma sample.

It is preferred that the plasma or serum sample has been obtained in a way, by which blood cells potentially containing augurin or precursors or fragments thereof are quantitatively separated from plasma or serum. This can be achieved for instance by centrifuging the blood sample at least at 2000 to 3000 g for at least 15 minutes.

Where appropriate, the sample may need to be homogenized, or extracted with a solvent prior to use in the present invention in order to obtain a liquid sample. A liquid sample hereby may be a solution or suspension. Liquid samples may be subjected to one or more pre-treatments prior to use in the present invention. Such pre-treatments include, but are not limited to dilution, filtration, centrifugation, concentration, sedimentation, precipitation, dialysis. Pre-treatments may also include the addition of chemical or biochemical substances to the solution, such as acids, bases, buffers, salts, solvents, reactive dyes, detergents, emulsifiers, chelators.

"Plasma" in the context of the present invention is the virtually cell-free supernatant of blood containing anticoagulant obtained after centrifugation. Exemplary anticoagulants include calcium ion binding compounds such as EDTA or citrate and thrombin inhibitors such as heparinates or hirudin. Cell-free plasma can be obtained by centrifugation of the anticoagulated blood (e.g. citrated, EDTA or heparinized blood) for at least 15 minutes at 2000 to 3000 g.

As outlined above, the present invention also pertains to an antibody or antigen-binding fragment or derivative thereof which is directed against an epitope comprised in the sequence spanning amino acid residues 71 to 107, preferably 71 to 100, more preferably 71 to 95, even more preferably 71 to 90, even more preferably 71 to 88, most preferably 71 to 83 and 79 to 88 of pre-augurin (SEQ ID NO:1). Preferred antibodies are described herein below. The invention further relates to the use of the antibodies or antigen-binding fragments or derivatives thereof as described herein in a sandwich immunoassay format for the detection and/or quantification of augurin or a fragment thereof in a biological sample from a bodily fluid. Such a fragment at least comprises a sequence spanning the two epitopes against which the two antibodies are directed, e.g. the kit can be used for the detection and/or quantification of augurin, argilin, Δ16-augurin and Δ16-argilin.

In the context of the antibodies, kits and immunoassays of the present invention, the antibody or antigen-binding fragment or derivative thereof, which is directed against an epitope comprised in the sequence spanning amino acid residues 71 to 107, preferably 71 to 100, more preferably 71 to 95, even more preferably 71 to 90, even more preferably 71 to 88, most preferably 71 to 83 and 79 to 88 of pre-augurin (SEQ ID NO:1), is a polyclonal, a monoclonal or a genetically engineered monoclonal antibody. Preferably, the antibody or antigen-binding fragment or derivative thereof is a monoclonal antibody.

The antibody or antigen-binding fragment or derivative thereof, which is directed against an epitope comprised in the sequence spanning amino acid residues 71 to 107, preferably 71 to 100, more preferably 71 to 95, even more preferably 71 to 90, even more preferably 71 to 88, most preferably 71 to 83 and 79 to 88 of augurin, is preferably an IgG or is derived from IgG.

The monoclonal antibodies according to the present invention may preferably be produced by a hybridoma cell line that is deposited at the DSMZ under accession number DSM ACC3206, DSM ACC3207, DSM ACC3208, DSM ACC3209, DSM ACC3210 or DSM ACC3211. These cell lines produce particular monoclonal antibodies directed against an epitope comprised in the sequence spanning amino acid residues 71 to 88 of pre-augurin according to the invention. The hybridoma cell line producing monoclonal antibody AK 482/H7 has been deposited at the Deutsche Sammlung von Mikroorganismen und Zellkulturen GmbH (DSMZ) on Jul. 3, 2013 under accession number DSM ACC3210. The hybridoma cell line producing monoclonal antibody AK 482/H2 has been deposited at the Deutsche Sammlung von Mikroorganismen und Zellkulturen GmbH (DSMZ) on Jul. 3, 2013 under accession number DSM ACC3208. The hybridoma cell line producing monoclonal antibody AK 482/G9 has been deposited at the Deutsche Sammlung von Mikroorganismen und Zellkulturen GmbH (DSMZ) on Jul. 3, 2013 under accession number DSM ACC3211. The hybridoma cell line producing monoclonal antibody AK 482/H10 has been deposited at the Deutsche Sammlung von Mikroorganismen und Zellkulturen GmbH (DSMZ) on Jul. 3, 2013 under accession number DSM ACC3209. The hybridoma cell line producing monoclonal antibody AK 439/F4 has been deposited at the Deutsche Sammlung von Mikroorganismen und Zellkulturen GmbH (DSMZ) on Jul. 3, 2013 under accession number DSM ACC3206. The hybridoma cell line producing monoclonal antibody AK 439/H10 has been deposited at the Deutsche Sammlung von Mikroorganismen und Zellkulturen GmbH (DSMZ) on Jul. 3, 2013 under accession number DSM ACC3207. All hybridoma cell lines have been produced according to the principles described herein above and in more detail in Example 1.

Finally, the invention also relates to hybridoma cell lines deposited at the DSMZ under accession numbers DSM ACC3206, DSM ACC3207, DSM ACC3208, DSM ACC3209, DSM ACC3210 and DSM ACC3211. These hybridoma cell lines produce the preferred antibodies of the present invention directed against amino acids 71 to 88 of pre-augurin, particularly amino acids 71 to 83 and 79 to 88 of pre-augurin.

The antibodies or antigen-binding fragments or derivatives thereof produced by the above described hybridoma cells can all be used in the immunoassay methods of the invention or can be comprised in the kits according to the invention.

In a specific aspect of the immunoassays or kits of the invention, the first antibody is a monoclonal antibody directed against amino acids 79-88 of pre-augurin and the second antibody is a monoclonal antibody directed against amino acids 71-83 of pre-augurin. For instance, the combination of the anti-AUG-EL10 antibody AK 482/H7 and the anti-PQW14 antibody AK 439/F4 is preferred. For instance, the anti-PQW14 antibody AK 439/F4 could be used as tracer antibody and the anti-AUG-EL10 antibody AK 482/H7 could be used as a solid phase antibody in a sandwich ELISA assay.

Monoclonal antibodies against the PQW14 peptide (SEQ ID NO:9) (amino acids 71-83 of pre-augurin) include the herein described antibodies AK 439/F4 and AK 439/H10. Monoclonal antibodies against the AUG-EL10 peptide (SEQ ID NO: 10) (corresponding to amino acids 79-88 of pre-augurin) include the herein described antibodies AK 482/H7, AK 482/H2, AK 482/G9 and AK 482/H10.

In a specific embodiment the invention relates to an immunoassay method for the detection of augurin or a precursor or fragment thereof comprising the steps of (a) contacting a sample suspected of comprising augurin or a precursor or fragment thereof with a first monoclonal antibody or an antigen-binding fragment or derivative thereof specific for augurin or a precursor or fragment thereof under conditions allowing for the formation of a complex between augurin or a precursor or fragment thereof and said first antibody or antigen-binding fragment or derivative thereof, (b) contacting said sample with a second monoclonal antibody or an antigen-binding fragment or derivative thereof specific for augurin or a precursor or fragment thereof under conditions allowing for the formation of a ternary complex between augurin or a precursor or fragment thereof and said first and second antibodies or antigen-binding fragments or derivatives thereof,
wherein the first antibody or antigen-binding fragment or derivative thereof is a monoclonal antibody or antigen-binding fragment or derivative thereof directed against amino acids 79-88 of pre-augurin and the second antibody or antigen-binding fragment or derivative thereof is a monoclonal antibody or antigen-binding fragment or derivative thereof directed against amino acids 71-83 of pre-augurin, and (c) detecting said ternary complex. Preferably the immunoassay in this embodiment is a sandwich ELISA assay and even more preferably the anti-PQW14 antibody AK 439/F4 is used as the tracer antibody (the "second antibody") and the anti-AUG-EL10 antibody AK 482/H7 is used as a solid phase antibody (the "first antibody"). However, also other combinations of the antibodies described above can be used. For example, the anti-AUG-EL10 antibody AK 482/H7 can be used as the tracer antibody (the "second antibody") and the anti-PQW14 antibody AK 439/F4 can be used as a solid phase antibody (the "first antibody").

Sequences

The amino acid sequence of the precursor peptide of augurin (pre-augurin) is given in SEQ ID NO:1. Upon cleavage of an N-terminal signal peptide (30 amino acids) augurin is released which relates to amino acid residues 31 to 148 of the pre-augurin sequence. The amino acid sequence of augurin is given in SEQ ID NO:2. Ecilin relates to amino acid residues 31-68 of pre-augurin. The amino acid sequence of ecilin is given in SEQ ID NO:3. Argilin relates to amino acid residues 71-148 of pre-augurin. The amino acid sequence of Argilin is provided in SEQ ID NO:4. Augurin can also be cleaved into a C-terminal fragment named Δ16 (SEQ ID NO:5) which relates to the amino acid sequence 134-148 of pre-augurin and Δ16-(SEQ ID NO:5) which relates to the amino acid sequence 134-148 of pre-augurin and Δ16-augurin (SEQ ID NO:6) which relates to the amino acid sequence 31-130 of pre-augurin. Δ16-augurin can be further cleaved into Δ16-argilin which relates to the amino acid sequence 71-130 of pre-augurin and is given in SEQ ID NO:7.

The sequence of the immunization peptide PKE14 (amino acids 48-60 of pre-augurin) is provided in SEQ ID NO:8. The sequence of the immunization peptide PQW 14 (amino acids 71-83 of pre-augurin) is provided in SEQ ID NO:9. The sequence of the immunization peptide AUG-EL10 (amino acids 79-88 of pre-augurin) is provided in SEQ ID NO:10. The sequence of the immunization peptide PGY 14 (amino acids 91-103 of pre-augurin) is shown in SEQ ID NO:11. And the sequence of the immunization peptide PDI 14 (amino acids 117-129 of pre-augurin) is given as SEQ ID NO: 12. The amino acid sequence of the binding epitope of the monoclonal antibodies AK 439/F4 and AK 439/H10 is shown in SEQ ID NO:13. The amino acid sequence of the binding epitope of the monoclonal antibodies AK 482/H7 and AK 482/H2 is shown in SEQ ID NO:14. The amino acid sequence of the binding epitope of the monoclonal antibodies AK 482/G9 and AK 482/H10 is shown in SEQ ID NO:15. The amino acid sequence of the synthetic peptides PQP-61 (containing amino acids 71-131 of pre-augurin) and AUG-WF15 (containing amino acids 73-87 of pre-augurin) are shown in SEQ ID NO:16 and 17, respectively.

The sequences of the peptides used for the epitope mapping of the monoclonal antibodies (as listed in Table 1) are provided in SEQ ID NO:18 to SEQ ID NO: 37.

```
SEQ ID NO: 1 (amino acid sequence of pre-augurin):
  1    MAASPARPAV LALTGLALLL LLCWGPGGIS GNKLKLNLQK REAPVPTKTK

51    VAVDENKAKE FLGSLKRQKR QLWDRTRPEV QQWYQQFLYM GFDEAKFEDD

101    ITYWLNRDRN GHEYYGDYYQ RHYDEDSAIG PRSPYGFRHG ASVNYDDY

SEQ ID NO: 2 (amino acid sequence of augurin):
  1    GNKLKLMLQK REAPVPTKTK VAVDENKAKE FLGSLKRQKR QLWDRTRPEV

51    QQWYQQFLYM GFDEAKFEDD ITYWLNRDRN GHEYYGDYYQ RHYDEDSAIG

101    PRSPYGFRHG ASVNYDDY

SEQ ID NO: 3 (amino acid sequence of ecilin):
  1    GNKLKLMLQK REAPVPIKTK VAVDENKAKE FLGSLKRQ SEQ ID NO: 4 (amino acid sequence of argilin):
  1    QLWDRTRPEV QQWYQQFLYM GFDEAKFEDD ITYWLNRDRN GHEYYGDYYQ

51    RHYDEDSAIG PRSPYGFRHG ASVNYDDY

SEQ ID NO: 5 (amino acid sequence Δ16):
  1    PYGFRHGASV NYDDY

SEQ ID NO: 6 (amino acid sequence of Δ16-augurin):
  1    GNKLKLMLQK REAPVPTKTK VAVDENKAKE FLGSLKRQKR QLWDRTRPEV

51    QQWYQQFLYM GFDEAKFEDD ITYWLNRDRN GHEYYGDYYQ RHYDEDSAIG

101    PRS
```

-continued

SEQ ID NO: 7 (amino acid sequence of Δ16-argilin):
  1   QLWDRTRPEV QQWYQQFLYM GFDEAKFEDD I7YWLNRDRN GHEYYGDYYQ
 51   RHYDEDSAIG PRS SEQ ID NO: 8 (amino acid sequence of PKE14)
  1   KTYVAVDENK AKE SEQ ID NO: 9 (amino acid sequence of PQW14)
  1   QLWDRTRPEV QQW SEQ ID NO: 10 (amino acid sequence of AUG-EL10)
  1   EVQQWYQQFL SEQ ID NO: 11 (amino acid sequence of PGY14)
  1   GFDEAKFEDD ITY SEQ ID NO: 12 (amino acid sequence of PDI14)
  1   DYYQRHYDED SAI SEQ ID NO: 13 (amino acid sequence 73-78 of pre-augurin)
  1   WDRTRP SEQ ID NO: 14 (amino acid sequence 82-87 of pre-augurin)
  1   QWYQQF SEQ ID NO: 15 (amino acid sequence 83-87 of pre-augurin)
  1   WYQQF SEQ ID NO: 16 (amino acid sequence of PQD-61):
  1   QLWDRTRPEV OQWYOQFLYM GFDEAKFEDD ITYWLNRDRN GHEYYGDYYQ
 51   RHYDEDSAIG P SEQ ID NO: 17 (amino acid sequence of AUG-WF15):
  1   WDRTRPEVQQ WYQQF SEQ ID NO: 18 (amino acid sequence 71-86 of pre-auqurin):
  1   QLWDRTRPEV QQWYQQ SEQ ID NO: 19 (amino acid sequence 73-86 of pre-augurin):
  1   WDRTRPEVQQ WYQQ SEQ ID NO: 20 (amino acid sequence 74-86 of pre-augurin):
  1   DRTRPEVQQW YQQ SEQ ID NO: 21 (amino acid sequence 73-86 of pre-augurin):
  1   RTRPEVQQWY QQ SEQ ID NO: 22 (amino acid sequence 76-86 of pre-augurin):
  1   TRPEVQQWYQ Q SEQ ID NO: 23 (amino acid sequence 68-82 of pre-augurin):
  1   QKRQLWDRTR PEVQQ SEQ ID NO: 24 (amino acid sequence 68-81 of pre-augurin):
  1   QKRQLWDRTR PEVQ SEQ ID NO: 25 (amino acid sequence 68-80 of pre-augurin):
  1   QKRQLWDRTR PEV SEQ ID NO: 26 (amino acid sequence 68-79 of pre-augurin):
  1   QKRQLWDRTR PE SEQ ID NO: 27 (amino acid sequence 76-88 of pre-augurin):
  1   TRPEVQQWYQ QFL SEQ ID NO: 28 (amino acid sequence 76-87 of pre-augurin):
  1   TRPEVQQWYQ QF SEQ ID NO: 29 (amino acid sequence 76-85 of pre-augurin):
  1   TRPEVQQWYQ SEQ ID NO: 30 (amino acid sequence 76-84 of pre-augurin):
  1   TRPEVQQWY -continued SEQ ID NO: 31 (amino acid sequence 76-83 of pre-augurin):
1   TRPEVQQW SEQ ID NO: 32 (amino acid sequence 79-91 of pre-augurin):
1   EVQQWYQQFL YMG SEQ ID NO: 33 (amino acid sequence 80-91 of pre-augurin):
1   VQQWYQQFLY MG SEQ ID NO: 34 (amino acid sequence 81-91 of pre-augurin):
1   QQWYQQFLYM G SEQ ID NO: 35 (amino acid sequence 82-91 of pre-augurin):
1   QWYQQFLYMG SEQ ID NO: 36 (amino acid sequence 83-91 of pre-augurin):
1   WYQQFLYMG SEQ ID NO: 37 (amino acid sequence 84-91 of pre-augurin):
1   YQQFLYMG

EXAMPLES

Example 1: Generation of Antibodies

Peptides

From the known amino acid sequence of human pre-augurin (see SEQ ID NO:1) five regions were selected, which were chemically synthesized by standard procedures (JPT GmbH, Berlin, Germany). These peptides were: PKE14 (amino acids 48-60 of pre-augurin, SEQ ID NO:8), PQW 14 (amino acids 71-83 of pre-augurin, SEQ ID NO:9), AUG-EL10 (amino acids 79-88 of pre-augurin, SEQ ID NO:10), PGY 14 (amino acids 91-103 of pre-augurin, SEQ ID NO: 11) and PDI 14 (amino acids 117-129 of pre-augurin, SEQ ID NO:12).

Development of Polyclonal Antibodies

Polyclonal antibodies directed against PKE14 (amino acids 48-60 of pre-augurin, SEQ ID NO:8), PQW 14 (amino acids 71-83 of pre-augurin, SEQ ID NO:9), PGY 14 (amino acids 91-103 of pre-augurin, SEQ ID NO: 11) and PDI 14 (amino acids 117-129 of pre-augurin, SEQ ID NO:12) were generated according to standard procedures (see EP 1488209 A1, EP 1738178 A1). In brief, peptides were coupled to the carrier protein KLH (Keyhole limpet hemocyanin) (PIERCE, Rockford, Ill., USA) using MBS (m-maleimidobenzoyl-N-hydroxysuccinimid Ester). With this conjugates sheep were immunized according to the following scheme: A sheep was initially immunized with 100 µg conjugate (mass refers to the peptide moiety of the conjugate) and boostered thereafter in four-weekly intervals with 50 µg conjugate each time. Four months after the initial immunization 300 ml antiserum were obtained from the sheep. Antigen-specific antibodies were purified from the respective antiserum as follows: 5 mg of the respective peptide was coupled to 5 ml SulfoLink-gel (PIERCE, Rockford, Ill., USA). 50 ml antiserum were incubated with the gel batchwise for 4 hours at room temperature. The material was transferred into a column (empty NAP25 column, Pharmacia). The flow through was discarded, the gel was washed with 100 ml wash buffer (100 mM K-phosphate, 0.1% Tween 20, pH 6.8), and specifically bound antibodies were eluted with 50 mM citric acid, pH 2.7. The eluate was dialysed against 50 mM Na-phosphate, 100 mM NaCl, pH 8.0.

Development of Monoclonal Antibodies

Monoclonal antibodies against PQW 14 (amino acids 71-83 of pre-augurin; SEQ ID NO:9) and AUG-EL10 (amino acids 79-88 of pre-augurin; SEQ ID NO: 10) were generated by standard procedures (Harlow E, Lane D. Antibodies—A Laboratory Manual. Cold Spring Harbor: Cold Spring Harbor Laboratory, 1988; Lane 1985. Journal of Immunology Methods 81:223-228): Briefly, peptides were conjugated to BSA by using Sulfo-MBS (m-maleimidobenzoyl-N-hydroxysuccinimid ester). With these conjugates Balb/c mice were immunized and boostered, and spleen cells were fused with SP2/0 myeloma cells to generate hybridoma cell lines. Cell lines were screened for their ability to secrete antibodies that would bind to the immunogenic peptides, which were coated on a solid polystyrene phase. With this approach, cell lines secreting monoclonal antibodies AK 439/F4 and AK 439/H10 (against PQW14) and AK 482/H7, AK 482/H2, AK 482/G9, AK 482/H10 (against AUG-EL10) were generated. For further experiments, monoclonal antibodies were purified from culture supernatant by Protein G affinity chromatography.

Labelling of Antibodies

Antibodies were labelled according to standard procedures (EP 1488209 A1, EP 1738178 A1): The concentration of the respective purified antibody was adjusted to 1 g/L, and the antibody was labeled by incubation with the chemiluminescent label MACN-Acridinium-NHS-Ester (1 g/L; InVent GmbH, Hennigsdorf, Germany) in a 1:5 molar ratio for 20 min at room temperature. The reaction was stopped by addition of 1/10 volume of 50 mmol/L glycine for 10 min at room temperature. Labeled antibody was separated from free label by size-exclusion chromatography on a NAP-5 column (GE Healthcare, Freiburg, Germany) and a Bio-Sil® SEC-400-5 HPLC column (BIO-RAD).

Coating of Antibodies

Antibodies were coated according to standard procedures (EP 1488209 A1, EP 1738178 A1): Polystyrene startubes (Greiner) were coated with purified antibody (per tube, 2 µg of antibody in 300 µL of 10 mmol/L Tris, 100 mmol/L NaCl, pH 7.8) overnight at 22° C. Tubes were then blocked with 10 mmol/L sodium phosphate (pH 6.5) containing 30 g/L Karion FP (Merck), 5 g/L bovine serum albumin protease free (Sigma) and lyophilized.

Example 2: Reference Augurin Assay Using Polyclonal Antibodies

Several sandwich immunoassays were set up using polyclonal components described above. All sandwich assays employing anti-PKE14 antibodies gave no signal with a plasma pool blood donor, whereas signals were seen in sandwich assays using anti-PQW14, anti-PGY14 and anti- PDI14 antibodies. The highest signal was obtained with anti-PQW14 as tracer antibody (directed against amino acids 71-83 of pre-augurin, SEQ ID NO:9) and anti-PDI14 as solid phase antibody (directed against amino acids 117-129 of pre-augurin, SEQ ID NO:12). Further experiments were conducted using this polyclonal antibody combination.

100 µl standards (recombinant human pre-augurin containing amino acids 1-148 [SEQ ID NO:1], Invivo BioTech Services GmbH, Hennigsdorf) or samples and 200 µl of buffer containing the MACN-labeled antibody were pipetted in the coated tubes (300 mM K-phosphate, pH 7.0, 50 mM NaCl, 10 mM EDTA, 0.09% Na-azide, 0.1% BSA, 0.1% unspecific bovine IgG, 0.1% unspecific. sheep-IgG, 0.01% unspecific mouse IgG, and contained $0.5 \times 10^6$ relative light units (RLU) of MACN-labeled antibody per 200 µl). The tubes were incubated 20 hours at room temperature under agitation. Then, the tubes were washed 4 times with 1 mL of B.R.A.H.M.S washing solution (Thermo Fisher Scientific, Clinical Diagnostics, B•R•A•H•M•S GmbH, Hennigsdorf, Germany), and bound chemiluminescence was measured for 1 s per tube with a LB952T luminometer (Berthold). Concentrations of samples were calculated using the Software MultiCalc (Spline Fit).

Example 3: Development of an Augurin Assay Using Monoclonal Antibodies

Several sandwich immunoassays were set up using monoclonal antibodies described above. All sandwich assays gave signals with a plasma pool blood donors using anti-PQW14 and anti-AUG-EL10 antibodies. The highest signal was obtained with anti-PQW14 antibody AK 439/F4 as tracer antibody and anti-AUG-EL10 antibody AK 482/H7 as solid phase antibody. Further experiments were conducted using this monoclonal antibody combination.

50 µl standards (recombinant human pre-augurin containing amino acids 1-148 [SEQ ID NO:1], Invivo BioTech Services GmbH, Hennigsdorf) or samples and 200 µl of buffer containing the MACN-labeled antibody were pipetted in the coated tubes (300 mM K-phosphate, pH 7.0, 50 mM NaCl, 10 mM EDTA, 0.09% Na-azide, 0.1% BSA, 0.1% unspecific bovine IgG, 0.1% unspecific. sheep-IgG, 0.01% unspecific mouse IgG, and contained $0.5 \times 10^6$ relative light units (RLU) of MACN-labeled antibody per 200 µl). The tubes were incubated 3 hours at room temperature under agitation. Then, the tubes were washed 4 times with 1 mL of B.R.A.H.M.S washing solution (Thermo Fisher Scientific, Clinical Diagnostics, B•R•A•H•M•S GmbH, Hennigsdorf, Germany), and bound chemiluminescence was measured for 1 s per tube with a LB952T luminometer (Berthold). Concentrations of samples were calculated using the Software MultiCalc (Spline Fit).

Example 4: Epitope Mapping of Monoclonal Antibodies

The mapping of epitopes within pre-augurin of the six monoclonal antibodies AK 439/F4, AK 439/H10, AK 482/H7, AK 482/H2, AK 482/G9 and AK 482/H10 was done using different peptides contained in the pre-augurin sequence that were synthesized with an additional spacer and a N-terminal or C-terminal biotin. 2 µg of the biotin-binding protein neutravidin (Thermo Scientific Pierce Protein Biology Products) per tube was coated as described above. 300 µl of peptide solution containing 50 ng of the respective peptide were pipetted per tube and incubated for 3 hours at room temperature under agitation. Then, the tubes were washed 4 times with 1 mL of B.R.A.H.M.S washing solution. 200 µl of antibody solution containing 50 ng of the respective antibody were incubated for 16 hours at room temperature under agitation and washed again 4 times as described above. To detect the potential binding of the monoclonal antibodies to the different peptides, 200 µl of a tracer solution containing goat-anti-mouse antibodies that were labelled with chemiluminescent MACN-Acridinium-NHS-Ester as described above, were incubated in the tubes for 2 hours at room temperature under agitation followed again by 4 washing steps and bound chemiluminescence was measured for 1 s per tube with a LB952T luminometer (Berthold).

Figure 2:
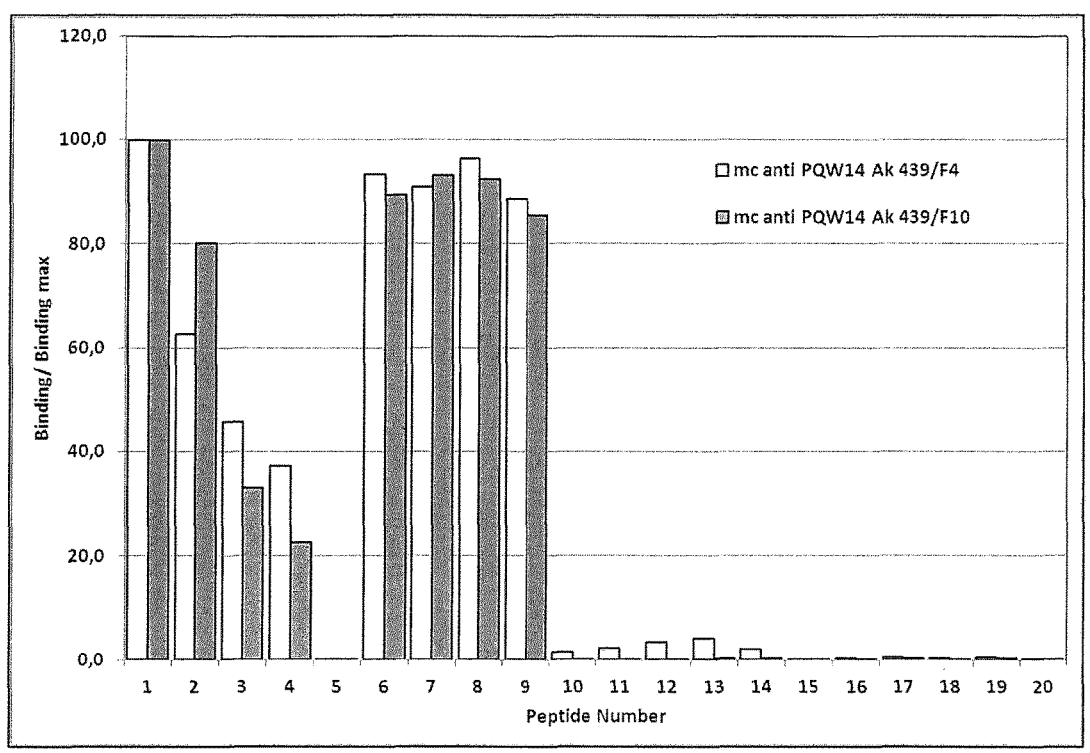
FIG. 2: Epitope mapping for the monoclonal antibodies raised against the immunization peptide PQW14 (SEQ ID NO:9), AK 439/F4 and AK 439/H10
Figure 3:
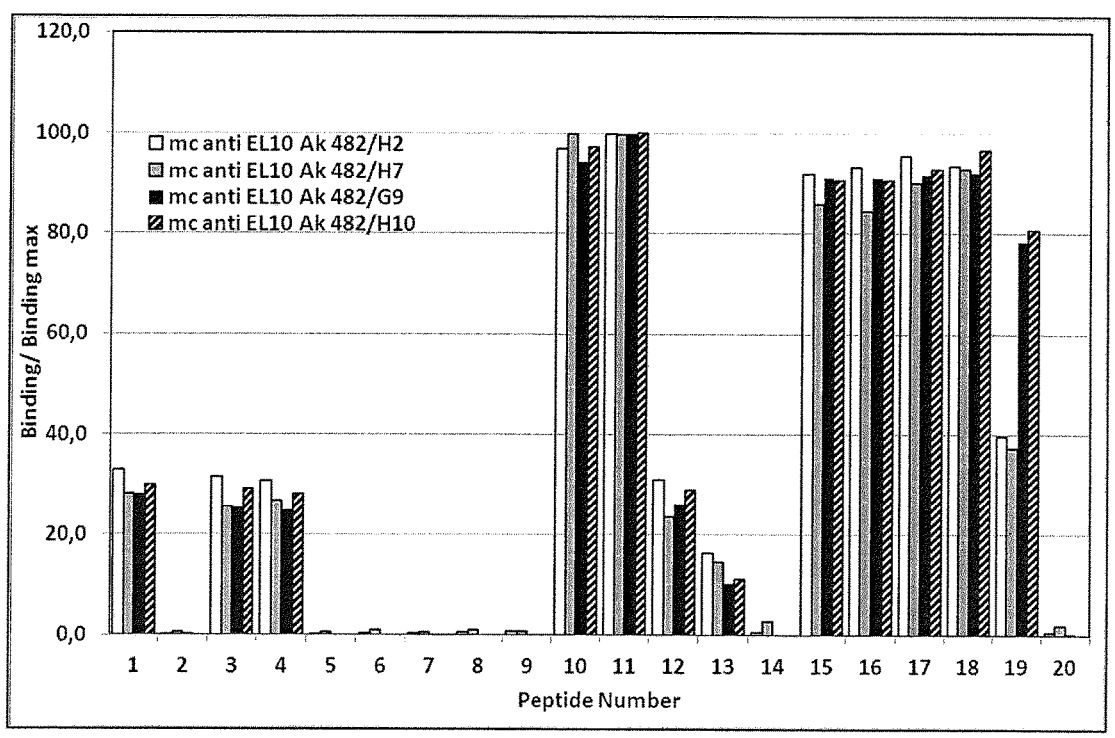
FIG. 3: Epitope mapping for the monoclonal antibodies raised against the immunization peptide AUG-EL10 (SEQ ID NO: 10), AK 482/H7, AK 482/H2, AK 482/G9 and AK 482/H10

The results of the epitope mapping are shown in Table 1. As shown in FIG. 2, the monoclonal antibodies AK 439/F4 and AK 439/H10 are binding to the same epitope consisting of the 6 amino acids 73-78 of the pre-augurin sequence (WDRTRP, SEQ ID NO: 13). FIG. 3 shows that the monoclonal antibodies AK 482/H7 and AK 482/H2 are binding to the same epitope consisting of the 6 amino acids 82-87 of the pre-augurin sequence (QWYQQF, SEQ ID NO: 14), whereas the monoclonal antibodies AK 482/G9 and AK 482/H10 are binding to the same epitope consisting of the 5 amino acids 83-87 of the pre-augurin sequence (WYQQF, SEQ ID NO: 15).

TABLE 1

Epitope mapping results: Observed binding signals for the two antibodies to the shown peptides representing subsequences of the pre-augurin sequence were related to the maximum binding obtained per antibody (B/Bmax).

| Peptide No. | Sequence | Monoclonal antibodies (B/Bmax in %) | | | | | |
| --- | --- | --- | --- | --- | --- | --- | --- |
| | | AK 439/F4 | AK 439/H10 | AK 482/H7 | AK 482/H2 | AK 482/G9 | AK 482/H10 |
| 1 | QLWDRTRPEVQQWYQQ | 100.0 | 100.0 | 28.2 | 32.8 | 28.1 | 30.0 |
| 2 | WDRTRPEVQQWYQQ | 62.6 | 80.1 | 0.7 | 0.3 | 0.4 | 0.3 |
| 3 | DRTRPEVQQWYQQ | 45.7 | 33.2 | 25.5 | 31.5 | 25.2 | 29.2 |
| 4 | RTRPEVQQWYQQ | 37.3 | 22.5 | 26.7 | 30.6 | 25.0 | 28.2 |
| 5 | TRPEVQQWYQQ | 0.1 | 0.1 | 0.5 | 0.3 | 0.3 | 0.3 |

TABLE 1-continued

Epitope mapping results: Observed binding signals for the two antibodies to the shown peptides representing subsequences of the pre-augurin sequence were related to the maximum binding obtained per antibody (B/Bmax).

| Peptide No. | Sequence | Monoclonal antibodies (B/Bmax in %) | | | | | |
|---|---|---|---|---|---|---|---|
| | | AK 439/F4 | AK 439/H10 | AK 482/H7 | AK 482/H2 | AK 482/G9 | AK 482/H10 |
| 6 | QKRQL<u>WDRTR</u>PEVQQ | 93.3 | 89.4 | 0.9 | 0.4 | 0.2 | 0.2 |
| 7 | QKRQL<u>WDRTR</u>PEVQ | 90.9 | 93.1 | 0.6 | 0.4 | 0.2 | 0.2 |
| 8 | QKRQL<u>WDRTR</u>PEV | 96.4 | 92.5 | 0.9 | 0.5 | 0.1 | 0.3 |
| 9 | QKRQL<u>WDRTR</u>PE | 88.7 | 85.5 | 0.7 | 0.7 | 0.2 | 0.2 |
| 10 | TRPEV<u>QQWYQQF</u>L | 1.5 | 0.2 | 100.0 | 97.0 | 94.4 | 97.3 |
| 11 | TRPEV<u>QQWYQQF</u> | 2.2 | 0.2 | 99.6 | 100.0 | 100.0 | 100.0 |
| 12 | TRPEV<u>QQ</u>WYQ | 3.4 | 0.2 | 23.5 | 30.9 | 26.2 | 29.2 |
| 13 | TRPEV<u>QQ</u>WY | 4.1 | 0.3 | 14.6 | 16.5 | 10.5 | 11.2 |
| 14 | TRPEV<u>QQ</u>W | 2.0 | 0.3 | 2.7 | 0.5 | 0.3 | 0.3 |
| 15 | EV<u>QQWYQQ</u>FLYMG | 0.2 | 0.2 | 86.0 | 92.0 | 91.2 | 90.7 |
| 16 | V<u>QQWYQQ</u>FLYMG | 0.4 | 0.3 | 84.5 | 93.2 | 91.2 | 90.7 |
| 17 | <u>QQWYQQ</u>FLYMG | 0.5 | 0.3 | 90.1 | 95.5 | 91.7 | 92.8 |
| 18 | <u>QWYQQ</u>FLYMG | 0.3 | 0.2 | 92.9 | 93.6 | 92.2 | 96.6 |
| 19 | <u>WYQQ</u>FLYMG | 0.6 | 0.4 | 37.2 | 39.7 | 78.4 | 80.8 |
| 20 | YQQFLYMG | 0.3 | 0.1 | 2.1 | 0.7 | 0.4 | 0.3 |

Figure 4:
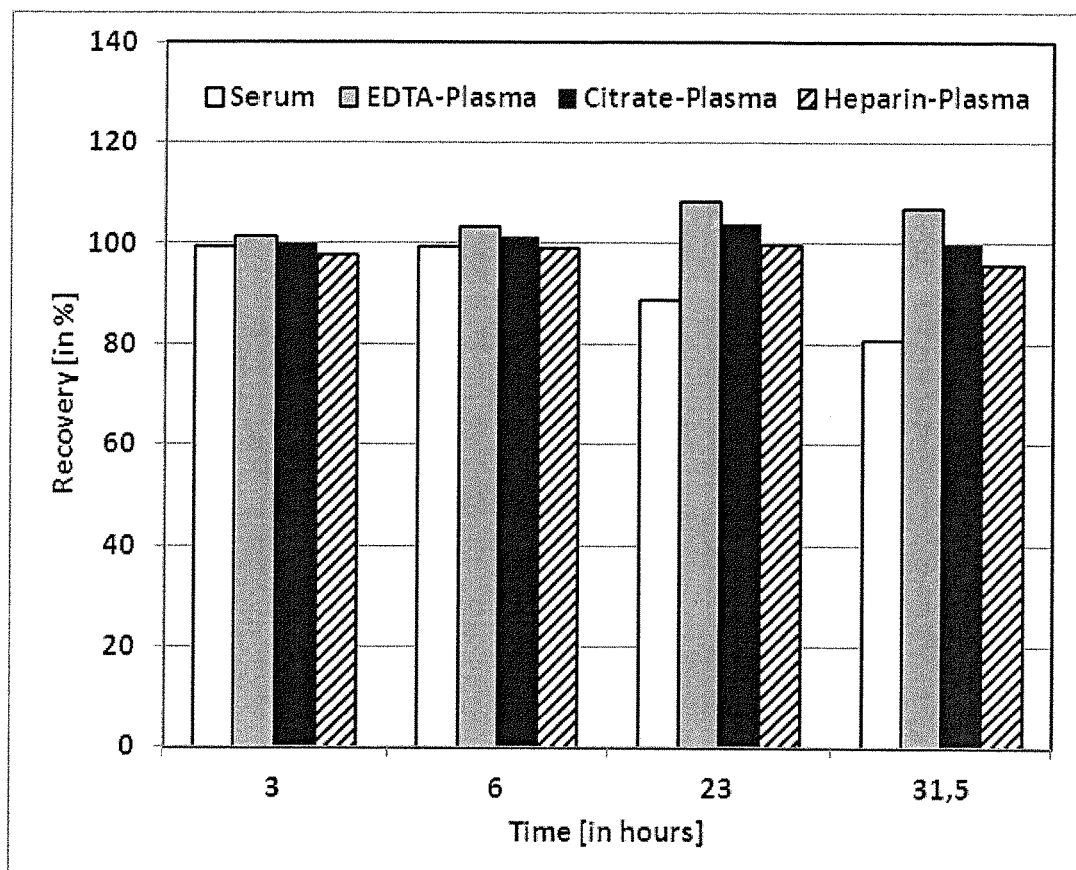
FIG. 4: Analyte stability. Shown are mean values (SEM) of ten samples from each matrix after storage at 22° C. for the indicated time periods in the relation to the values measured without having the samples stored (recovery in %) measured with the monoclonal immunoassay.

Example 5: Stability of the Analyte 10 samples each of four different matrices (serum, EDTA-, Citrate- and Heparin-Plasma) were stored for different time periods at 22° C. and then measured in batch with the monoclonal immunoassay. Time point 0 without storage at 22° C. was used as reference and set 100%. As shown in FIG. 4 serum is stable for 6 hours at room temperature with a 10% decline after 23 hours and 20% decline after 31.5 hours storage. The analyte was stable in EDTA-, Citrate- and Heparin-Plasma for at least 31.5 hours at 22° C.

Moreover, the stability of the analyte was tested after several freeze-thawing cycles. 10 EDTA-plasma samples from healthy blood donors were thawed and frozen up to seven times. The analyte was absolutely stable in EDTA-plasma after seven freeze-thawing cycles with no significant decline or increase in augurin immunoreactivity.

Example 6: Dose Response Curve

Figure 5:
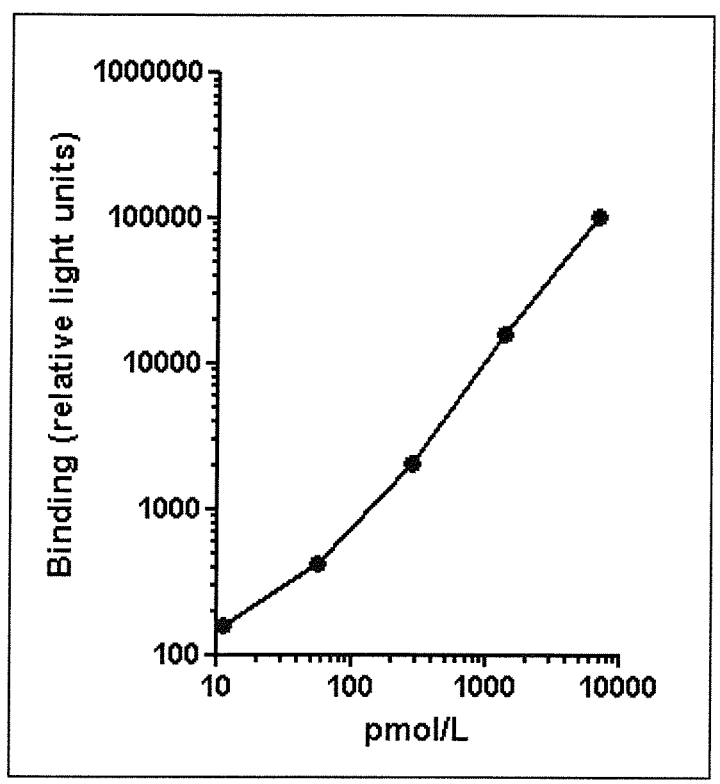
FIG. 5: Dose response curve for recombinant pre-augurin measured with the monoclonal immunoassay.

A dose response curve could be created by using the recombinant pre-augurin (SEQ ID NO: 1) as standard material in the monoclonal immunoassay as described above. A typical dose response curve is shown in FIG. 5.

Example 7: Augurin Immunoreactivity in a Healthy Population

Figure 6:
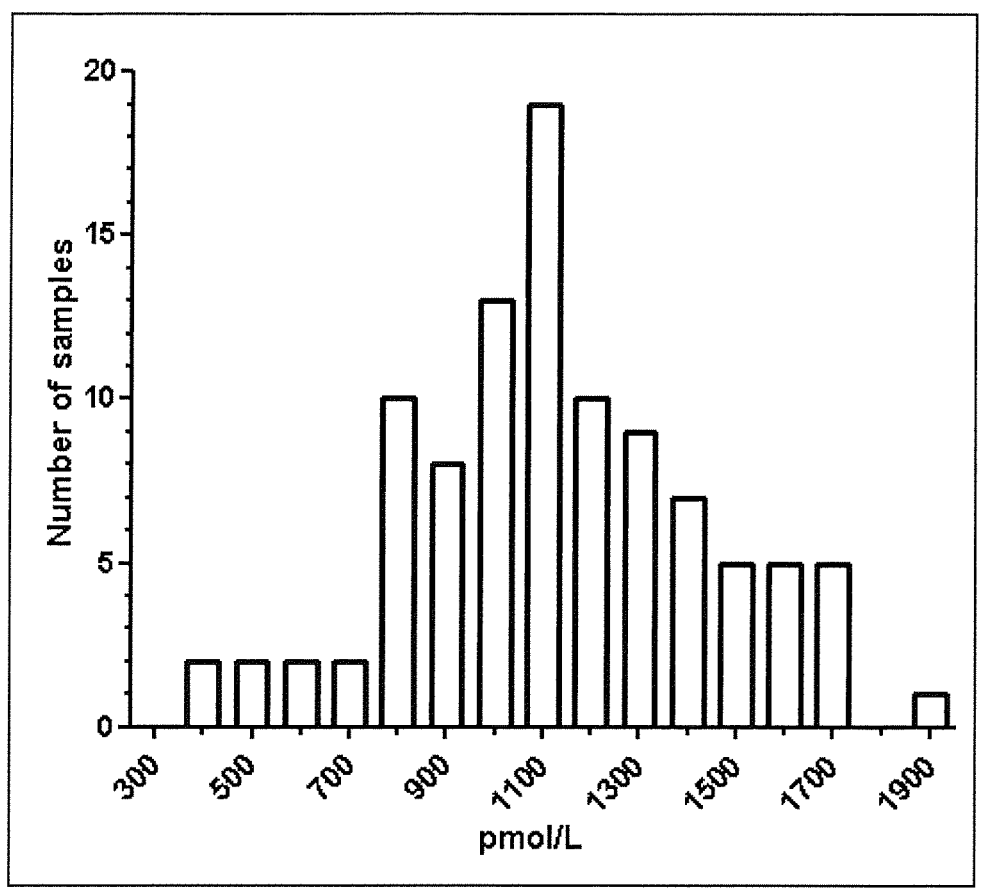
FIG. 6: Frequency distribution of augurin immunoreactivity in a healthy population (n=100) measured with the monoclonal immunoassay.

100 EDTA-plasma samples from healthy subjects were measured using the monoclonal immunoassay. The frequency distribution of the augurin immunoreactivity in these samples is shown in FIG. 6. Augurin immunoreactivity was measurable in all samples with a median value of 1119 pmol/L (95% CI 1071-1195) with a minimum value at 385 pmol/L and a maximum value at 1880 pmol/L. The $75^{th}$ and $97.5^{th}$ was at 1333 and 1744 pmol/L, respectively. Augurin immunoreactivity in women (n=64; median 1073 pmol/L) were significantly lower (p<0.01) when compared to the augurin immunoreactivity in men (n=36; median 1328 pmol/L). There was no correlation between augurin immunoreactivity and age (Spearman r=0.076, p>0.05).

Example 8: Comparison Between the Monoclonal Sandwich Immunoassay of the Present Invention and the Competitive Prepro-Augurin (71-107) Immunoassay from Phoenix Peptides as Well as the Reference Sandwich Immunoassay of Example 2

Figure 7:
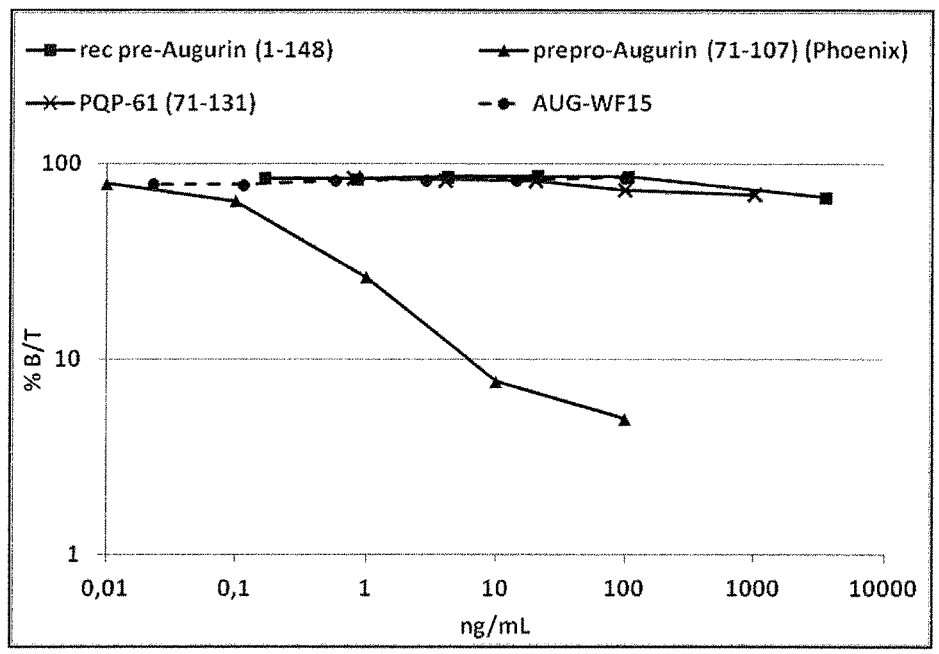
FIG. 7: Measurement of different standard materials with the competitive enzyme immunoassay prepro-augurin (71-107) from Phoenix Pharmaceuticals (A), the polyclonal reference sandwich immunoassay (B) and the monoclonal sandwich immunoassay (C).
Figure 7:
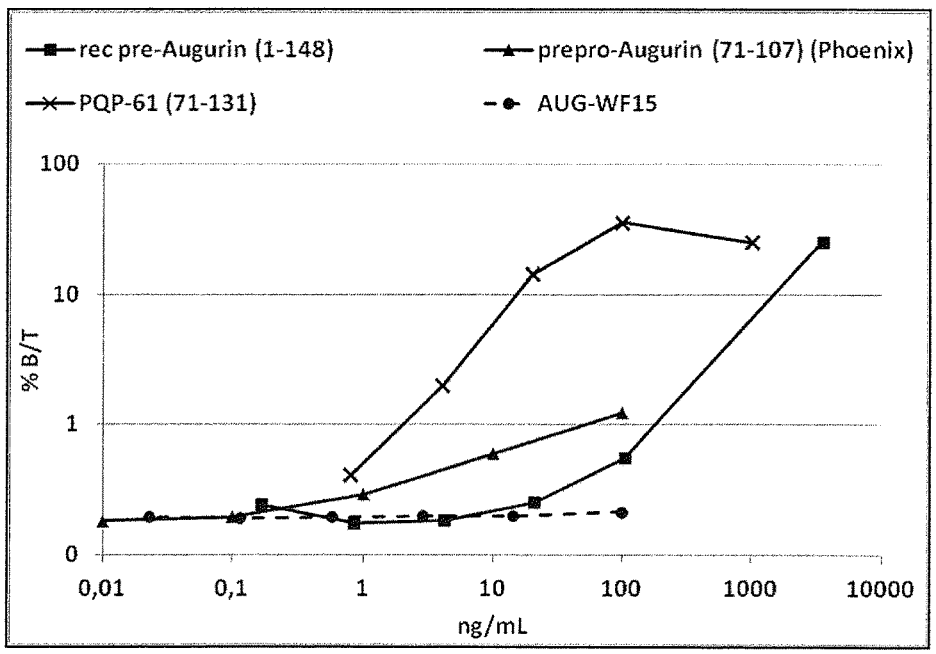
Figure 7:
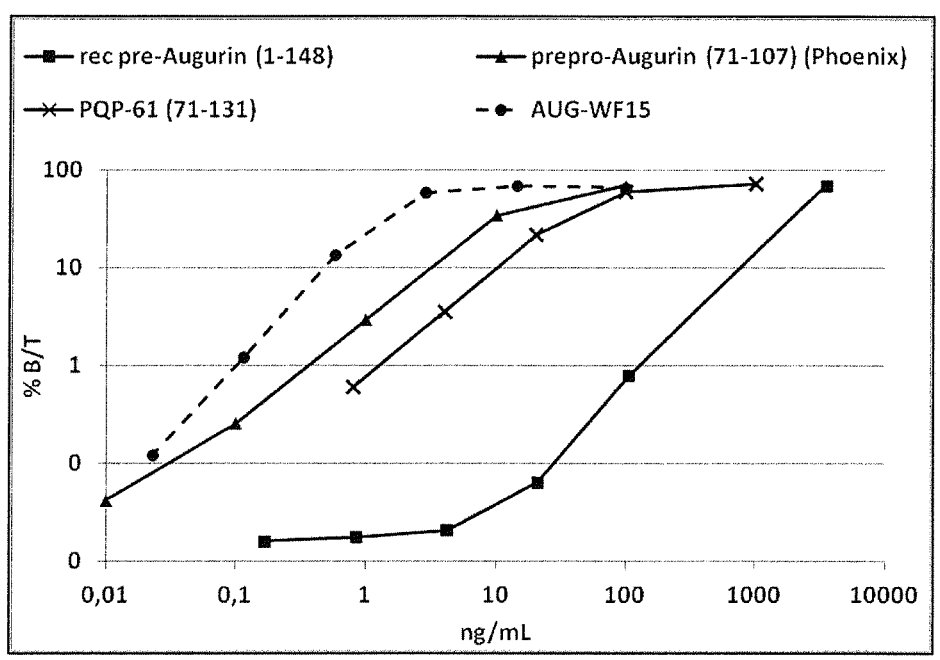

Different standard peptides were measured with the sandwich immunoassays of Examples 2 and 3 and the competitive human prepro-augurin (71-107) immunoassay (EK-012-22) from Phoenix Pharmaceuticals Inc. (Burlingame, USA). Four different standard peptides were used: recombinant human pre-augurin (amino acids 1-148; SEQ ID NO: 1), prepro-augurin (71-107)-peptide from Phoenix Pharmaceuticals Inc., synthetic peptide PQP-61 (containing amino acids 71-131 of pre-augurin, SEQ ID NO:16) and AUG-WF15 (containing amino acids 73-87 of pre-augurin, SEQ ID NO:17). The results are shown in FIGS. 7 A, B and C. The standard peptide prepro-augurin (71-107) but neither the recombinant pre-augurin (1-148) nor the peptides PQP-61 and AUG-WF15 were detected with the competitive enzyme immunoassay prepro-augurin (71-107) from Phoenix Pharmaceuticals (FIG. 7A). As this assay was developed for the detection of prepro-augurin (71-107) one would expect that at least the recombinant pre-augurin (1-148) and the peptide PQP-61 should be detectable because both peptides contain the amino acid sequence 71-107.

The recombinant pre-augurin (1-148) and the peptide PQP-61 but neither the peptide prepro-augurin (71-107) from Phoenix Pharmaceuticals nor the peptide AUG-WF15 were detected with the polyclonal reference sandwich immunoassay based on a combination of antibodies directed against amino acids 71-83 and 117-129 of pre-augurin, respectively) (Example 2, FIG. 7B). The solid phase antibody used in this immunoassay was raised against the peptide PDI14, which is directed against amino acids 117-129 of pre-augurin, and the peptides prepro-augurin (71-107) from Phoenix Pharmaceuticals and AUG-WF15 do not contain this epitope. Therefore, one has to expect that this polyclonal immunoassay is not able to detect these two peptides. In contrast, as the recombinant pre-augurin (1-148) and the peptide PQP-61 do contain both epitopes against the two peptides PQW14 and PDI14 that were used for raising the two polyclonal antibodies, it has to be expected that they are detectable with this assay.

All four standard peptides were detectable with the sandwich immunoassay using two monoclonal antibodies as described in the present application (FIG. 7 C; Example 3), which was as expected because the epitopes of the two monoclonal antibodies are contained in all four standard peptides.

Figure 8:
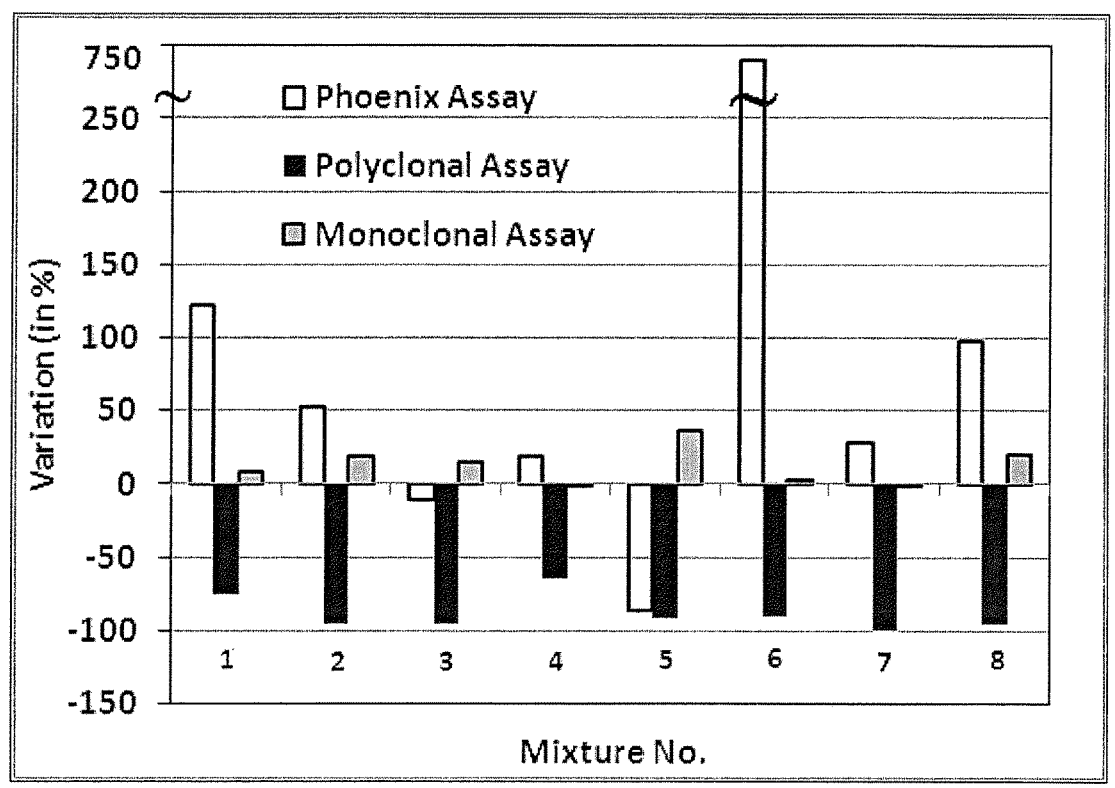
FIG. 8 shows the variations of the results of Table 2.

Possible interferences of the accuracy of analyte detection ware tested in EDTA-plasma samples from healthy blood donors. 16 EDTA-plasma samples were measured separately as well as a 1:1 mixture of 2 respective samples. The 16 EDTA-plasma samples and the 8 mixture samples were measured with the polyclonal and monoclonal immunoassay of Examples 2 and 3 as well as with the prepro-augurin (71-107) assay from Phoenix Pharmaceuticals. The measuring values of the samples and sample mixtures as well as the calculated mixture values and the respective variations are given in Table 2. The variations of the results are also shown in FIG. 8. The prepro-augurin (71-107) assay from Phoenix Pharmaceuticals showed deviations for the mixtures from −85.5 up to 737.3%. Only two of the 8 mixture samples were below 20% deviation between the calculated and the measured sample mixture values. With the reference immunoassay of Example 2 all 8 mixture values are significantly below the respective calculated sample value (range −65.1 to 100.0%). In contrast, the monoclonal immunoassay of Example 3 according to the invention showed only slight deviations between the calculated and the measured mixture value (range −1.0 to 35.8%) with only one mixture value with a deviation of more than 20%.

All samples (standard peptide samples, patient samples, mixture samples) were measured in duplicate and the mean value is given as the result. None of the samples measured with the monoclonal immunoassay of Example 3 and only 20% of the samples measured with the polyclonal immunoassay of Example 2 showed a variation coefficient of >10%, whereas 80% of the samples measured with the from 24 measured with the prepro-augurin (71-107) assay from Phoenix Pharmaceuticals showed a variation coefficient of >10%. Therefore, samples cannot be measured reliably with the prepro-augurin (71-107) assay from Phoenix Pharmaceuticals.

Taken together these results clearly show that a reliable measurement of augurin immunoreactivity is only possible by using the immunoassay according to the present invention making use of two antibodies against an epitope in residues 71-107 of pre-augurin.

TABLE 2

Results of variations for mixture EDTA-plasma samples

Competitive prepro-augurin (71-107) assay from Phoenix Pharmaceuticals

| Mixture | Sample A (ng/ml) | Sample B (ng/ml) | ½ (Sample A + B) calculated (ng/ml) | ½ (Sample A + B) measured (ng/ml) | Variation calculated/ measured (in %) |
| --- | --- | --- | --- | --- | --- |
| 1 | 4.53 | 0.66 | 2.60 | 5.77 | 122.3 |
| 2 | 7.56 | 1.70 | 4.63 | 7.06 | 52.6 |
| 3 | 4.89 | 0.91 | 2.90 | 2.57 | −11.4 |
| 4 | 8.04 | 1.54 | 4.79 | 5.71 | 19.2 |
| 5 | 16.44 | 0.62 | 8.53 | 1.24 | −85.5 |
| 6 | 1.39 | 0.68 | 1.03 | 8.67 | 737.4 |
| 7 | 5.68 | 1.12 | 3.40 | 4.35 | 27.8 |
| 8 | 2.38 | 0.89 | 1.64 | 3.25 | 98.5 |

| Mixture | Sample A (pmol/L) | Sample B (pmol/L) | ½ (Sample A + B) calculated (pmol/L) | ½ (Sample A + B) measured (pmol/L) | Variation calculated/ measured (in %) |
| --- | --- | --- | --- | --- | --- |

Reference polyclonal immunoassay for detection of augurin immunoreactivity (Example 2)

| 1 | 19.6 | 180.9 | 100 | 24.5 | −75.6 |
| 2 | 8.5 | 679.1 | 344 | 15.6 | −95.5 |
| 3 | 20.6 | 1470.5 | 746 | 31.2 | −95.8 |
| 4 | 7.6 | 59.1 | 33 | 11.6 | −65.1 |
| 5 | 35.7 | 619.2 | 327 | 29.7 | −90.9 |
| 6 | 45.9 | 334.7 | 190 | 19.9 | −89.5 |
| 7 | 0.0 | 779.1 | 390 | 0 | −100.0 |
| 8 | 18.0 | 780.8 | 399 | 17.7 | −95.6 |

TABLE 2-continued

Results of variations for mixture EDTA-plasma samples

Monoclonal immunoassay for detection of augurin immunoreactivity (Example 3)

| 1 | 1057 | 630  | 844  | 906  | 7.4  |
|---|------|------|------|------|------|
| 2 | 768  | 1043 | 905  | 1074 | 18.6 |
| 3 | 2758 | 2884 | 2821 | 3238 | 14.8 |
| 4 | 1185 | 1005 | 1095 | 1091 | -0.3 |
| 5 | 921  | 1385 | 1153 | 1566 | 35.8 |
| 6 | 794  | 247  | 520  | 536  | 2.9  |
| 7 | 1166 | 1285 | 1225 | 1214 | -1.0 |
| 8 | 312  | 1315 | 813  | 973  | 19.7 |

---

The invention claimed is:

1. An immunoassay method for the detection of augurin or a precursor or fragment thereof comprising
   (a) contacting a sample suspected of comprising augurin or a precursor or fragment thereof with a first antibody or an antigen-binding fragment thereof specific for augurin or a precursor or fragment thereof and a second antibody or an antigen-binding fragment thereof specific for augurin or a precursor or fragment thereof under conditions allowing for the binding of the two antibodies or antigen-binding fragments thereof to augurin or a precursor or fragment thereof,
   wherein said first and second antibodies or antigen-binding fragments thereof are specific for epitopes contained within the sequence spanning amino acids 71 to 107 of pre-augurin according to SEQ ID NO:1,
   wherein said first and second antibodies or antigen-binding fragments thereof are specific for different and non-overlapping epitopes,
   wherein the first antibody or antigen-binding fragment is produced by a hybridoma cell line selected from the group consisting of cell line 482/H2 deposited as DSM ACC3208, cell line 482/H10 deposited as DSM ACC3209, cell line 482/H7 deposited as DSM ACC3210, and cell line 482/G9 deposited as DSM ACC3211, and wherein the second antibody or antigen-binding fragment is produced by hybridoma cell line 439/F4 deposited as DSM ACC3206 or hybridoma cell line 439/H10 deposited as DSM ACC3207, and (b) detecting the binding of the first and second antibodies or antigen-binding fragments thereof to augurin or a precursor or fragment thereof.

2. An immunoassay method for the detection of augurin or a precursor or fragment thereof comprising
 (a) contacting a sample suspected of comprising augurin or a precursor or fragment thereof with a first antibody or an antigen-binding fragment thereof specific for augurin or a precursor or fragment thereof under conditions allowing for the formation of a complex between augurin or a precursor or fragment thereof and said first antibody or antigen-binding fragment thereof,
 (b) contacting said sample with a second antibody or an antigen-binding fragment thereof specific for augurin or a precursor or fragment thereof under conditions allowing for the formation of a ternary complex between augurin or a precursor or fragment thereof and said first and second antibodies or antigen-binding fragments thereof,
 wherein said first and second antibodies or antigen-binding fragments thereof are specific for epitopes contained within the sequence spanning amino acids 71 to 107 of pre-augurin according to SEQ ID NO:1,
 wherein said first and second antibodies or antigen-binding fragments thereof are specific for different and non-overlapping epitopes,
 wherein the first antibody or antigen-binding fragment is produced by a hybridoma cell line selected from the group consisting of cell line 482/H2 deposited as DSM ACC3208, cell line 482/H10 deposited as DSM ACC3209, cell line 482/H7 deposited as DSM ACC3210, and cell line 482/G9 deposited as DSM ACC3211, and
 wherein the second antibody or antigen-binding fragment is produced by hybridoma cell line 439/F4 deposited as DSM ACC3206 or hybridoma cell line 439/H10 deposited as DSM ACC3207, and
 (c) detecting said ternary complex.

3. The immunoassay method according to claim 1, wherein said epitopes are not more than 6 amino acids apart.

4. The immunoassay method according to claim 3, wherein said first and second antibodies or antigen-binding fragments thereof are specific for epitopes contained within the sequence spanning amino acids 71 to 88 according to SEQ ID NO:1 and wherein said epitopes are not more than 3 amino acids apart.

5. The immunoassay method according to claim 1, wherein the first antibody or antigen-binding fragment thereof is specific for an epitope contained within the sequence spanning amino acids 71 to 83 of pre-augurin according to SEQ ID NO:1 and wherein the second antibody or antigen-binding fragment thereof is specific for an epitope contained within the sequence spanning amino acids 79 to 88 of pre-augurin according to SEQ ID NO:1.

6. The immunoassay method according to claim 1, wherein the sample is a derived from a bodily fluid or tissue of a subject.

7. The immunoassay method according to claim 1, wherein the immunoassay is a sandwich ELISA assay.

8. The immunoassay method according to claim 1, wherein the first antibody or the antigen-binding fragment thereof is a solid phase antibody that is attached a solid phase and the second antibody or the antigen-binding fragment thereof is a tracer antibody labelled with a detection probe, or vice versa.

9. The immunoassay method according to claim 8, wherein the solid phase is a bead, a surface of a well or a container, a chip, and/or a strip.

10. The immunoassay method according to claim 8, wherein the detection probe is a dye, a radioisotope, and/or a reactive or catalytically active moiety.

* * * * *